(12) United States Patent
Hover et al.

(10) Patent No.: US 6,783,529 B2
(45) Date of Patent: Aug. 31, 2004

(54) NON-METAL INSERTS FOR BONE SUPPORT ASSEMBLY

(75) Inventors: Anne Hover, Playa Del Rey, CA (US); Roy Sanders, Tampa, FL (US); Donald Martin Sturgeon, Wilmington, DE (US); Jerry Lower, Bourbon, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 10/013,306

(22) Filed: Oct. 19, 2001

(65) Prior Publication Data

US 2002/0173792 A1 Nov. 21, 2002

Related U.S. Application Data

(63) Continuation-in-part of application No. 09/575,764, filed as application No. PCT/US00/09582 on Apr. 10, 2000, now Pat. No. 6,709,436, which is a continuation-in-part of application No. 09/289,324, filed on Apr. 9, 1999, now Pat. No. 6,296,645.

(51) Int. Cl.⁷ ............................................. A61B 17/72
(52) U.S. Cl. ...................................................... 606/62
(58) Field of Search ........................ 606/53, 60, 62–73, 606/76

(56) References Cited

U.S. PATENT DOCUMENTS

| | | | |
|---|---|---|---|
| 2,136,471 A | 11/1938 | Schneider | 128/92 |
| 2,987,062 A | 6/1961 | Ellison | 128/92 |
| 3,272,204 A | 9/1966 | Artandi et al. | 128/334 |
| 3,463,158 A | 8/1969 | Schmitt et al. | 128/334 |
| 3,531,561 A | 9/1970 | Trehu | |
| 3,596,656 A | 8/1971 | Kante | 128/92 |
| 3,636,956 A | 1/1972 | Schneider | |
| 3,739,773 A | 6/1973 | Schmitt et al. | |

(List continued on next page.)

FOREIGN PATENT DOCUMENTS

| | | | |
|---|---|---|---|
| DE | 1 949 923 | 4/1971 | |
| EP | 0 491 983 A1 | 7/1992 | |
| FR | 2 710 835 | 4/1995 | |
| SU | 1692566 | 11/1991 | |
| WO | WO 9841161 A2 * | 9/1998 | .......... A61B/17/72 |

OTHER PUBLICATIONS

Brochure of Intramedullary Nail.
One–Nail . . . Diaphyseal Fractures.
System Introduction, The Titanium Unreamed Tibial Nail System.

(List continued on next page.)

*Primary Examiner*—David O. Reip
*Assistant Examiner*—Jessica R. Baxter
(74) *Attorney, Agent, or Firm*—Shewchuk IP Services; Jeffrey D. Shewchuk

(57) ABSTRACT

A bone support structure is formed with opposing dynamization windows, and spacers of a bioresorbable material are positioned within the dynamization windows. The dynamization windows are longer than they are wide. The spacers may be integrally formed as a single insert. The bone support assembly is used with a bone fastener such as a bone screw which is advanced transversely through both the insert and the bone. The bone fastener is smaller across than the dynamization windows, so each spacer spaces the bone fastener relative to its dynamization window. As the spacers resorb, stress (at least in one direction) is increasingly transmitted through the fracture site rather than through the bone support structure. The positioning of the bone fastener, the shape and size of the dynamization windows and spacers, and the material of the spacers all allow design control over the type and amount of dynamization seen at the fracture site. Also, because the bone fastener is smaller across than the dynamization windows and spacers, a larger error in placement of the bone fastener is permissible. The insert can be selected by the surgeon and placed into the bone support structure based upon desired treatment modalities.

28 Claims, 9 Drawing Sheets

U.S. PATENT DOCUMENTS

| | | |
|---|---|---|
| 3,892,649 A | 7/1975 | Phillips et al. .............. 204/181 |
| 3,902,497 A | 9/1975 | Casey |
| 3,918,100 A | 11/1975 | Shaw et al. ..................... 3/1.9 |
| 3,937,223 A | 2/1976 | Roth |
| 3,960,151 A | 6/1976 | Kuhn |
| 4,146,936 A | 4/1979 | Aoyagi et al. ................ 3/1.91 |
| 4,186,448 A | 2/1980 | Brekke |
| 4,192,021 A | 3/1980 | Deibig et al. ..................... 3/1.9 |
| 4,279,249 A | 7/1981 | Vert et al. ..................... 128/92 |
| 4,280,233 A | 7/1981 | Raab ............................ 3/1.91 |
| 4,292,694 A | 10/1981 | Koeneman ..................... 3/1.91 |
| 4,338,926 A | 7/1982 | Kummer et al. .............. 129/92 |
| 4,429,690 A | 2/1984 | Angelino-Pievani |
| 4,457,301 A | 7/1984 | Walker ........................ 128/92 |
| 4,523,591 A | 6/1985 | Kaplan et al. |
| 4,550,449 A | 11/1985 | Tunc ............................ 623/16 |
| 4,612,923 A | 9/1986 | Kronenthal .................. 128/92 |
| 4,655,203 A | 4/1987 | Törmälä et al. .............. 128/92 |
| 4,733,654 A | 3/1988 | Marino ........................ 128/92 |
| 4,756,307 A | 7/1988 | Crowninshield ............ 128/92 |
| 4,781,183 A | 11/1988 | Casey et al. |
| 4,790,302 A | 12/1988 | Colwill et al. ................ 128/92 |
| 4,851,008 A | 7/1989 | Johnson ....................... 623/16 |
| 4,863,475 A | 9/1989 | Andersen et al. ............ 623/16 |
| 4,875,474 A | 10/1989 | Border ........................ 128/92 |
| 4,895,572 A | 1/1990 | Chernott |
| 4,898,186 A | 2/1990 | Ikada et al. .................... 606/62 |
| 4,911,153 A | 3/1990 | Border ........................ 606/98 |
| 4,919,666 A | 4/1990 | Buchhorn et al. ............ 623/16 |
| 4,943,292 A | 7/1990 | Foux ............................ 606/70 |
| 4,968,317 A | 11/1990 | Tormalla et al. .............. 606/77 |
| 4,973,333 A | 11/1990 | Treharne ..................... 606/77 |
| 5,009,664 A * | 4/1991 | Sievers ........................ 606/60 |
| 5,057,110 A | 10/1991 | Kranz et al. |
| 5,057,111 A | 10/1991 | Park ............................ 606/69 |
| 5,084,050 A | 1/1992 | Draenert ..................... 606/77 |
| 5,084,051 A | 1/1992 | Tormala et al. .............. 606/77 |
| 5,108,399 A | 4/1992 | Eitenmuller et al. ......... 606/77 |
| 5,112,333 A | 5/1992 | Fixel |
| 5,127,913 A | 7/1992 | Thomas, Jr. ................. 606/62 |
| 5,190,546 A | 3/1993 | Jervis |
| 5,236,431 A | 8/1993 | Gogolewski ................. 606/72 |
| 5,275,601 A | 1/1994 | Gogolewski et al. |
| 5,292,695 A | 3/1994 | Galloway .................... 502/53 |
| 5,413,577 A | 5/1995 | Pollock |
| 5,484,438 A | 1/1996 | Pennig |
| 5,514,137 A | 5/1996 | Coutts ......................... 606/62 |
| 5,569,250 A | 10/1996 | Saver et al. |
| 5,603,715 A | 2/1997 | Kessler |
| 5,618,286 A | 4/1997 | Brinker |
| 5,741,266 A | 4/1998 | Moran et al. .................. 606/96 |
| 5,743,914 A * | 4/1998 | Skiba ........................... 606/73 |
| 5,776,194 A | 7/1998 | Mikol et al. ................... 623/16 |
| 5,792,400 A | 8/1998 | Talja et al. ................. 264/103 |
| 5,810,821 A | 9/1998 | Vandewalle .................. 606/65 |
| 5,836,949 A | 11/1998 | Campbell, Jr. |
| 5,855,579 A | 1/1999 | James et al. |
| 5,868,746 A | 2/1999 | Sarver et al. ................. 606/69 |
| 5,871,484 A | 2/1999 | Spievack et al. ............. 606/60 |
| 5,895,390 A | 4/1999 | Moran et al. .................. 606/96 |
| 5,928,267 A | 7/1999 | Bonutti et al. ............. 606/216 |
| 5,935,127 A | 8/1999 | Border ........................ 606/62 |
| 6,004,323 A | 12/1999 | Park et al. .................... 606/61 |
| 6,168,595 B1 * | 1/2001 | Durham et al. ............... 606/64 |
| 6,443,954 B1 * | 9/2002 | Bramlet et al. ............... 606/62 |
| 2002/0151898 A1 * | 10/2002 | Sohngen et al. .............. 606/62 |

OTHER PUBLICATIONS

Craig B. Ordway, Surgical Technique, AIM Titanium Femoral Nail System, New York, pps. 1–11.

Biomet Inc., Vector Intertrochanteric Nail, Version Two, 18 pages, 1995. U.S.A.

Biomet Inc., Biomet Retrograde Femoral Nail, 6 pages, 1995 U.S.A.

Biomet Inc., Biomet Retrograde Femoral Nail Surgical Technique, 12 pages, 1995. U.S.A.

Biomet Inc., UNIFLEX® Hummeral Nail Surgical Technique, 14 pages, 1997. U.S.A.

Biomet Inc. UNIFLEX® Femoral Nail Surgical Technique, 18 pages, 1996. U.S.A.

Biomet Inc., Titanium Femoral Interlocking Nail, 16 pages, 1995. U.S.A.

Biomet Inc., Vector Intertrochanteric Nail, Version One, 16 pages, 1995. U.S.A.

Biomet Inc., UNIFLEX™ Tibial Nail System, 4 pages, 1995. U.S.A.

Biomet Inc., UNIFLEX® Family Nailing System, 16 pages, 1995. U.S.A.

Orthopaedic Equipment Co., Inc. "They Through He Wouldn't Make The Tournament", 1 page, Publ. 1976.

H. McKellp et al., Development and Clinical Performance Of A Reversible Titanium Alloy Femoral Intramedullary Nail, 16 pages, 1991. U.S.A.

Ferguson, Wyss and Pichora, "Finite Element Stress Analysis of a Hybrid Fracture Fixation Plate", Medical Engineering & Physics, vol. 18, No. 3, pp. 241–250, Apr., 1996.

Yeadon, Foux, Uhthoff, and Russell, "Influence of Axially Flexible Plates on Bone Healing: A Biomechanical Study in Canine Femora", CMBES 20 CCGB, pp. 34–35, 1994.

Simon, Ricci, and Di Cesare, "Bioresorbable Fracture Fixation in Orthopedics: A Comprehensive Review. Part II. Clinical Studies", American Journal of Orthopedics, pp. 754–762, Nov. 1997.

Kato, Latta, and Malinin, "The Weakest Link in the Bone—Plate—Fracture System: Changes with Time", Clinical and Laboratory Performance of Bone Plates, ASTM STP 1217, ed. by Harvey and Games, pp. 85–94, 1994.

Hazre and Lin, "Theoretical Strength Comparison of Bioabsorbable (PLLA) Plates and Conventional Stainless Steel and Titanium Plates Used in Internal Fracture Fixation", Clinical and Laboratory Performance of Bone Plates, ASTM STP 1217, ed. by Harvey and Games, pp. 53–64, 1994.

Räihä, "Biodegradable Implants as Intramedullary Nails. A Survey of Recent Studies and an Introduction to their Use," Clinical Materials, vol. 10, pp. 35–39, 1992.

Foux, Yeadon, and Uhthoff, "Improved Fracture Healing with Less Rigid Plates: A Biomechanical Study in Dogs", Clinical Orthopaedics and Related Research, ed. by Brighton, No. 339, pp. 232–245, 1997.

* cited by examiner

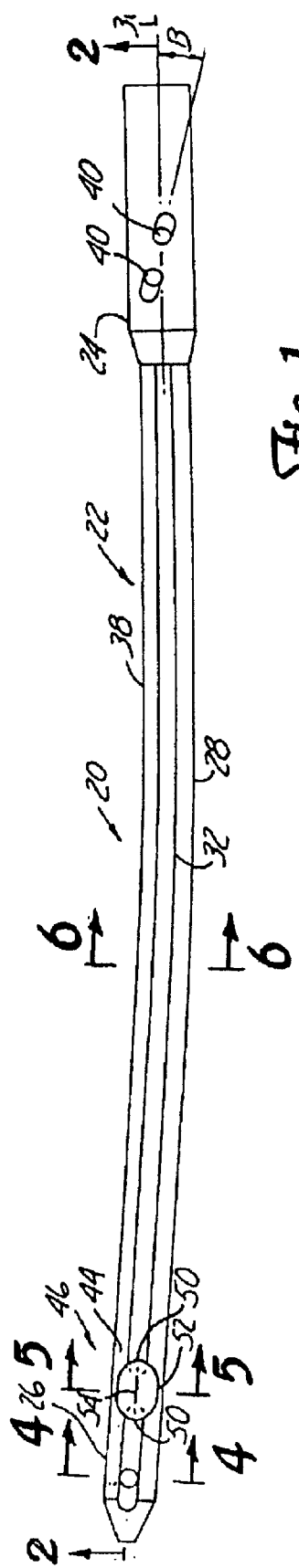
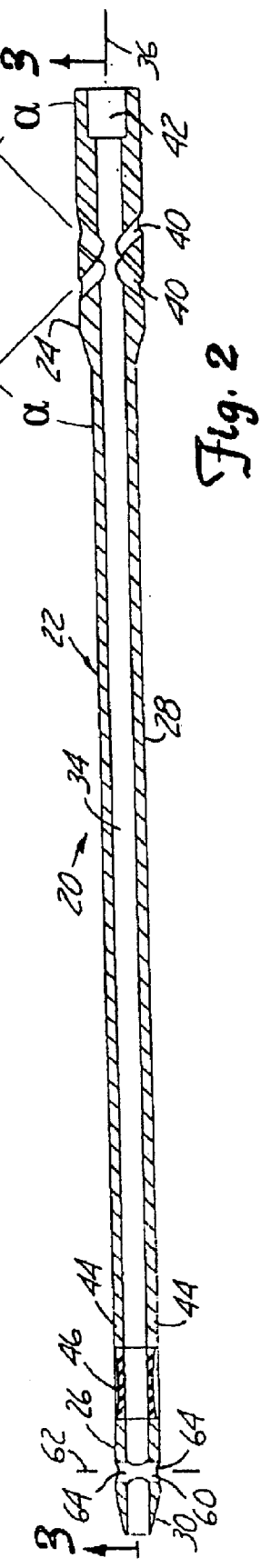
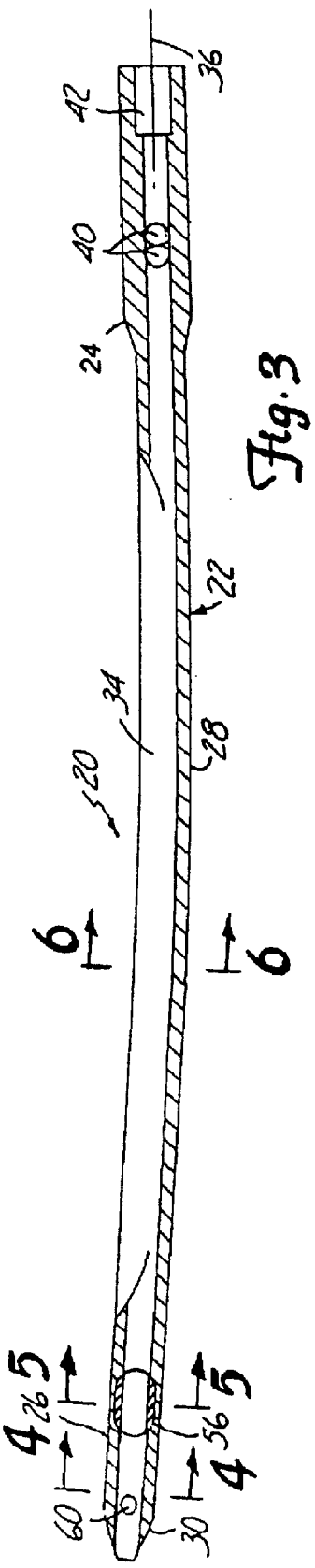
Fig. 1
Fig. 2
Fig. 3

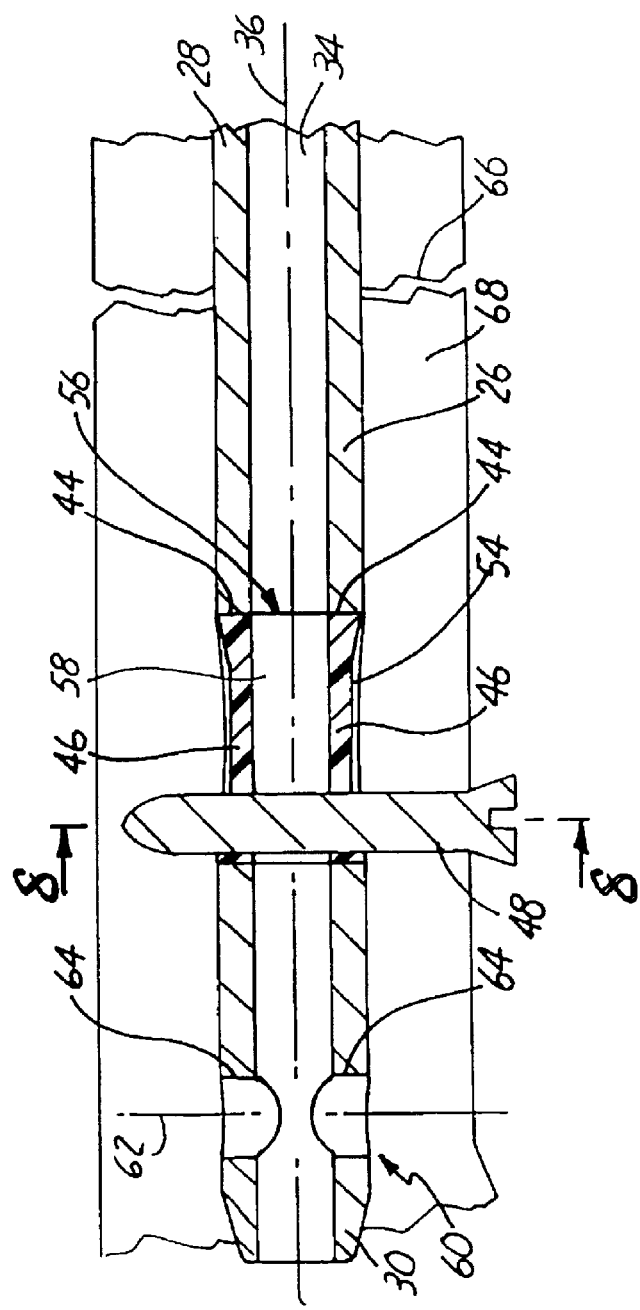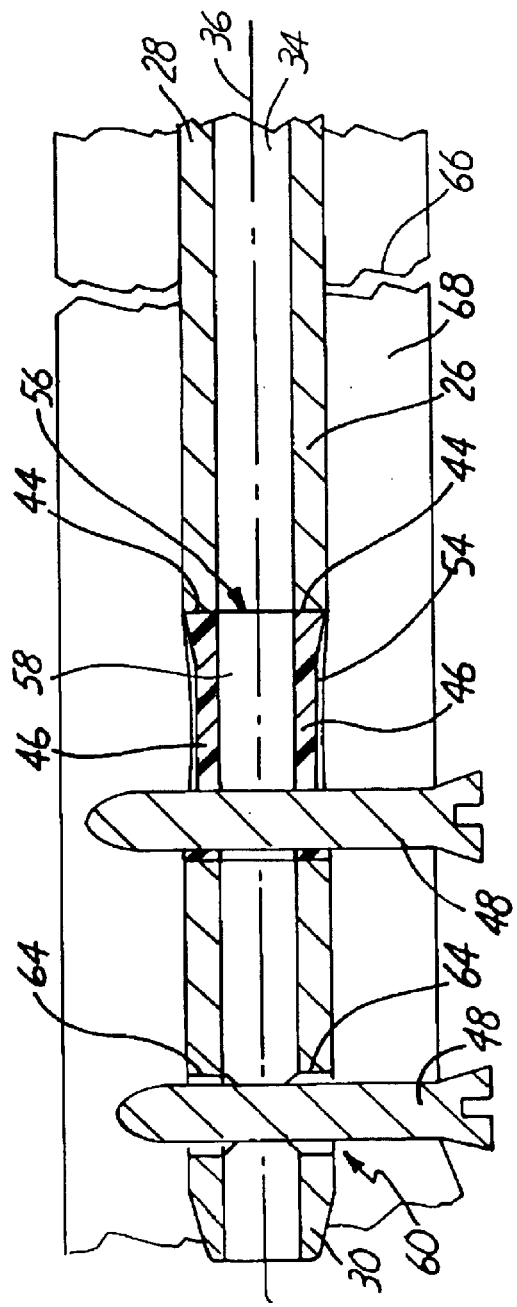

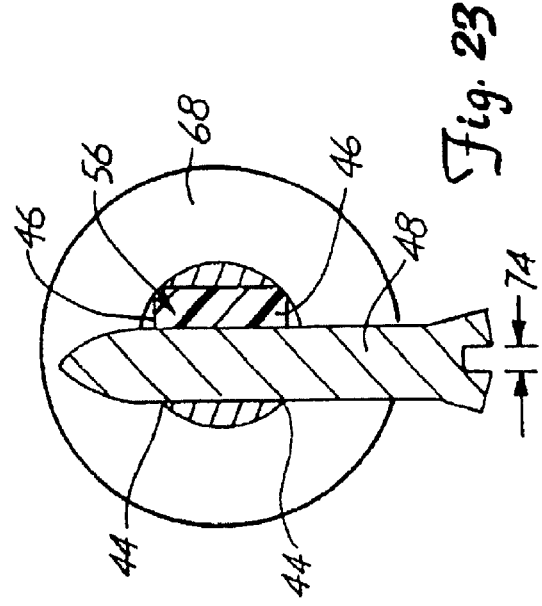
Fig. 22
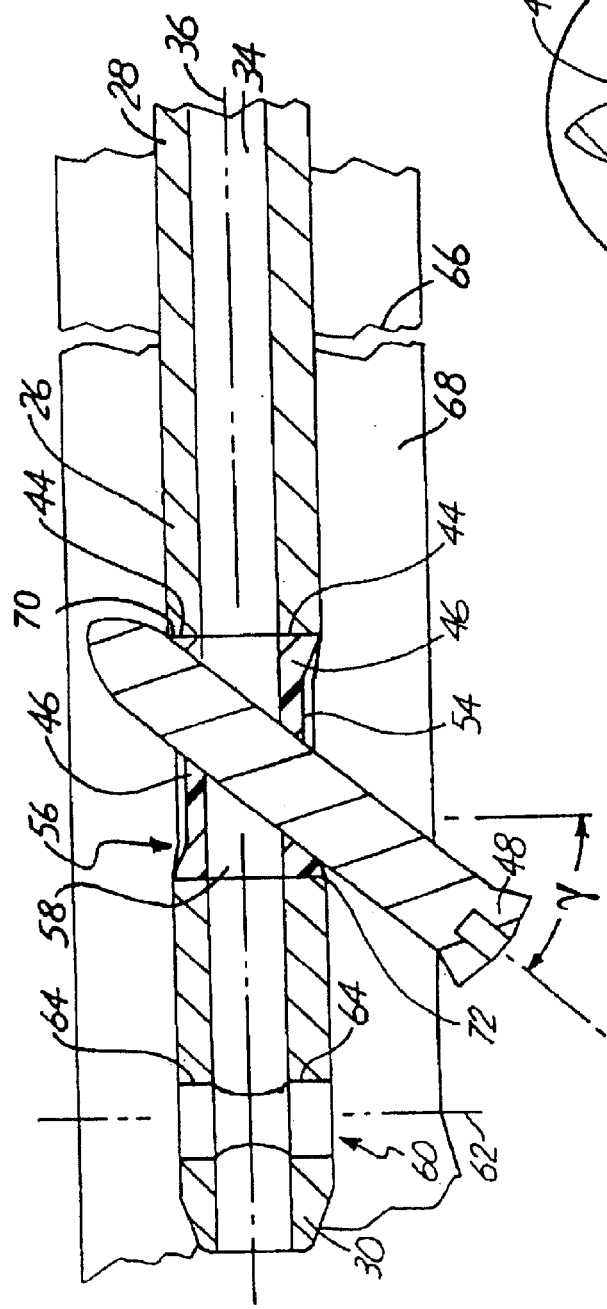
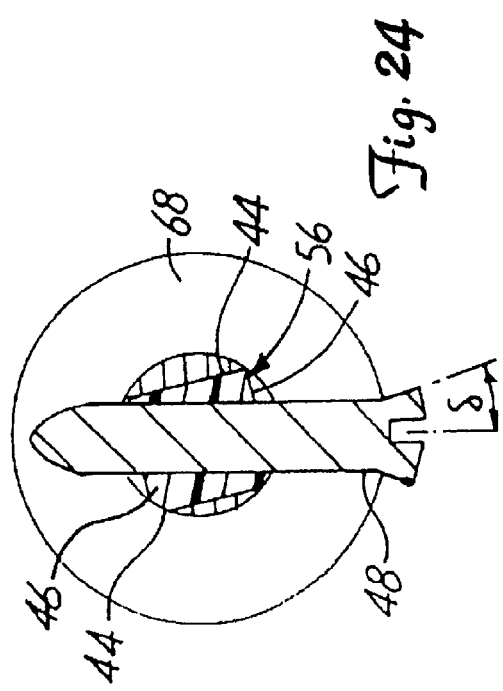
Fig. 23
Fig. 24

NON-METAL INSERTS FOR BONE SUPPORT ASSEMBLY

CROSS-REFERENCE TO RELATED APPLICATION(S)

This application is a Continuation-in-Part of U.S. application Ser. No. 09/575,764, filed May 22, 2000 now U.S. Pat. No. 6,709,436 and entitled NON-METAL SPACERS FOR INTRAMEDULLARY NAIL, which is a continuation of PCT application no. PCT/US00/09582, filed Apr. 10, 2000, which is a Continuation-in-Part of U.S. application Ser. No. 09/289,324, filed Apr. 9, 1999, entitled INTRAMEDULLARY NAIL WITH NON-METAL SPACERS, now issued as U.S. Pat. No. 6,296,645.

BACKGROUND OF THE INVENTION

The present invention relates to intramedullary nails used for treatment of a fracture of a bone having a medullary canal extending longitudinally within the bone, and particularly to the structure of the intramedullary nail and methods for anchoring the intramedullary nail with respect to one or more fragments of the fractured bone. The present invention also relates to bone plates used for treatment of a fracture of a bone placed upon the surface of one or more fragments of the fractured bone, and to similar bone support structures which are used to anchor or support two portions of bone relative to one another.

Intramedullary nails are used by orthopedic surgeons to treat fractures involving long bones such as the femur, humerus, tibia, fibula, etc. The medullary canal of the fractured bone is drilled out or otherwise opened from one end, and the intramedullary nail is longitudinally placed within the medullary canal to contact at least two fragments, i.e., such that the nail extends on both sides of the fracture. As used herein, the term "fragment" refers to a portion of a fractured bone regardless of whether the fracture is complete. When implanted, the nail strengthens and supports fragments of the fractured bone during healing of the fracture.

Various types of intramedullary nails are well known within the medical device arts, and several different methods have been used to attach the intramedullary nail within the bone. For instance, in U.S. Pat. No. 4,338,926 to Kummer et al., an intramedullary nail is disclosed which places a compressive force radially outward on the interior wall of the cortex structure surrounding the intramedullary nail. The compressive force secures the Kummer nail within the medullary canal of the fragments. Similarly, in U.S. Pat. No. 4,457,301 to Walker a flexible plastic core elements holds longitudinal pins of an intramedullary nail in place. In U.S. Pat. No. 5,514,137 to Coutts, cement is injected through a cannula in an intramedullary nail to secure the distal end of the intramedullary nail to the bone. Other intramedullary nail designs employ a more secure and mechanically positive attachment to the bone, such as through use of one or more bone fasteners which extend transversely to the longitudinal axis of the nail and through the cortex of the bone. The bone fastener is received within a receiving recess or through-hole within the intramedullary nail to secure the intramedullary nail relative to the bone fastener. In the transverse attachment, the receiving opening defines an axis which is at an angle to the longitudinal axis of the nail (90° and 45° angles are common), and the bone fastener is advanced on this receiving opening axis. U.S. Pat. No. 4,733,654 to Marino, U.S. Pat. No. 5,057,110 to Kranz et al., U.S. Pat. No. 5,127,913 to Thomas, Jr., U.S. Pat. No. 5,514,137 to Coutts (proximal end) and others disclose such a transverse bone fastener attachment in a bicortical attachment. U.S. Pat. No. 5,484,438 to Pennig shows a nail design with a recess which permits only unicortical attachment. The present invention particularly relates to intramedullary nails which use bone fasteners transversely through the cortex for attachment.

Bone plates are used by orthopedic surgeons to treat many types of bones, to support two portions of bone relative to one another. The bone plate is positioned to extend from one portion of bone to the other portion of bone, typically in direct contact with both bone portions. For instance, the bone plate may be positioned such that the plate extends on both sides of a fracture. The bone plate is separately secured to each of the supported bone portions, such as by bone screws. When implanted, the bone plate supports tension, compression and/or bending stresses from one portion of bone to the other.

Problems may arise when attaching an intramedullary nail or bone plate to a fragment or other bone portion with a bone fastener. It is occasionally difficult for the surgeon to properly align the bone fastener and/or a hole for the bone fastener with the receiving opening on the nail or plate. Part of the error is unique to intramedullary nails, due to difficulty in aligning the bone fastener with the receiving opening when the receiving opening is within the bone. Additionally, the nail may be slightly bent during insertion of the nail structure into the medullary canal. Such bending of the nail structure may be desired in some instances so the nail shape better matches the particular shape of the medullary canal for a particular patient. Regardless of whether intended or unintended, bending of the nail structure creates further alignment errors between the bone fastener and/or a hole for the bone fastener and the receiving opening on the nail. Other alignment difficulties are common to both bone plates and intramedullary nails. For example, other bones, bony growths, or overlying tissue may make placement of the intramedullary nail or bone plate and insertion of the bone screws difficult. Four types of alignment errors can be identified: (a) in transverse displacement (e.g., when the axis of the bone fastener is in the same transverse plane as the receiving opening in the nail/plate but does not intersect the longitudinal central axis of the nail/plate), (b) in longitudinal displacement (i.e., when the bone fastener is at a different longitudinal location than the receiving opening in the nail/plate), (c) in longitudinal angular misaligned (i.e., when the axis of the receiving opening and the axis of the bone fastener are at different angles relative to the longitudinal axis of the nail/plate), and (d) in transverse angular misaligned (i.e., when the axis of the receiving opening and the axis of the bone fastener are in the same transverse plane but at different radial positions relative to the nail/plate).

Various types of jigs have been proposed to reduce alignment errors, such as shown in U.S. Pat. No. 4,733,654 to Marino and U.S. Pat. No. 5,776,194 to Mikol et al. Primarily used with intramedullary nails, the jig may be temporarily attached to the proximal end of the nail to help align the bone fastener and/or the drill to the receiving opening in the nail. While such jigs are helpful, they become less reliable as distance from the proximal end of the nail increases, particularly if any bending of the intramedullary nail has occurred. Though less commonly used with bone plates, jigs can be used to position a drill and/or a bone fastener relative to the holes in the bone plate. Additional solutions are needed, especially for attaching the distal end of the intramedullary nail to a distal fragment.

A second method to reduce such alignment problems is to locate the receiving openings in-situ, such as through an x-ray or through the use of magnets as taught in U.S. Pat. No. 5,127,913 to Thomas, Jr. Such methods are not typically preferred by surgeons in as much as they require significant additional time and effort during the orthopedic surgery, to the detriment of the patient.

A third method to reduce such alignment problems is to drill the receiving opening into the bone plate or intramedullary nail only after the plate or nail is positioned relative to the bone, allowing the receiving opening to be formed at a range of locations. Such in-situ drilling is taught in U.S. Pat. No. 5,057,110 to Kranz et al., wherein a tip section of the intramedullary nail is formed of a bioresorbable material. However, bioresorbable materials are not as strong as metals, ceramics or other materials, leading to a product which is weaker than desired and has a weaker attachment than desired.

Further problems occur during placement of the bone plate or intramedullary nail. For minimal damage to cortical tissue of the bone and most beneficial healing using an intramedullary nail, both the hole that is drilled in the medullary canal for the nail and then the nail itself need to be precisely located and secured with respect to the medullary canal. For bone plates, the surface contour of the bone or other tissue may not allow the bone plate to be positioned exactly as desired, such as bone surface contours which do not allow the bone plate to be in full contact with the bone throughout the length of the bone plate.

Additional problems with bone support structures occur due to the healing requirements of the bone with respect to the strength and rigidity of the nail/plate. U.S. Pat. No. 4,756,307 to Crowninshield and U.S. Pat. No. 4,338,926 to Kummer et al. disclose intramedullary nails with bioresorbable portions to weaken the nail relative to the bone over time, but these nails forsake the use of a transverse bone fastener to achieve this benefit.

U.S. Pat. No. 5,935,127 to Border and French Patent Publication No. 2,710,835 to Medinov disclose at least partially filling the opening in a bone support device with an amount of resorbable material. However, both of these devices appear to be fully assembled during manufacture. That is, neither of these devices leave the surgeon with flexibility in whether and when to place the the resorbable material into the opening, or in any selection as to the type of resorbable material to be used. Also, both the Border patent and the Medinov patent fail to consider how to adequately and optimally secure the resorbable material to the bone support device.

BRIEF SUMMARY OF THE INVENTION

The present invention involves a bone support implant to treatment of a bone. The bone support implant is formed with at least one window in an exterior side, and an insert of a non-metal material is selected and positioned within the window. The bone support implant is used with a bone fastener such as a bone screw which is advanced transversely through the insert in the implant and through the bone. In one aspect of the invention, the non-metal insert is formed of a bioresorbable material, and the window is a dynamization window. As the bioresorbable insert resorbs, stress is increasingly transmitted through the fracture site rather than through the bone support implant. The positioning of the bone fastener, the shape and size of the window and insert, and the material of the insert all allow control over the type and amount of dynamization seen at the fracture site. Use of a separate insert, which is placed into the implant structure by a treating physician, allows selection of a non-metal insert which has appropriate features and/or had been appropriately treated and handled to best match the desired healing modality of the particular fracture.

BRIEF DESCRIPTION OF THE DRAWINGS

FIG. 1 is an elevational view of an intramedullary nail in accordance with the present invention.

FIG. 2 is a cross-sectional view taken along lines 2—2 in FIG. 1.

FIG. 3 is a cross-sectional view taken along lines 3—3 in FIG. 2.

FIG. 18 is a cross-sectional view of a distal end of the nail of FIGS. 1–6 in a first type of attachment to a bone.

FIG. 20 is a cross-sectional view of a distal end of the nail of FIGS. 1–6 in a second type of attachment to a bone.

FIG. 22 is a cross-sectional view of a distal end of the nail of FIGS. 1–6 in a fourth type of attachment to a bone.

FIG. 23 is a cross-sectional view similar to FIG. 19 showing a first type of permissible offset.

FIG. 24 is a cross-sectional view similar to FIG. 19 showing a second type of permissible offset.

Figure 4:
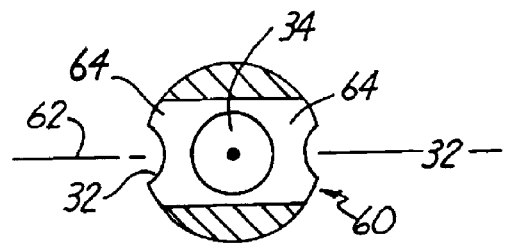
FIG. 4 is a cross-sectional view taken along lines 4—4 in FIGS. 1 and 3.

While the above-identified drawing figures set forth one or more preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

An intramedullary nail 20 according to the present invention includes a nail structure 22 with a proximal end 24, a distal end 26 and a shaft 28, with "proximal" and "distal" being defined in accordance with the direction the nail 20 is intended to be inserted into the bone. As known in the art, the dimensions of the proximal end 24, the distal end 26 and the shaft 28 may be selected based on the required strength of the nail and the intended use of the intramedullary nail. The nail 20 depicted in FIGS. 1–11 and 13–24 is generally sized and shaped for treating a fracture toward the middle of an otherwise healthy adult human femur. If desired, the nail 20 may be included in a kit having various sizes of nails to fit the femurs of variously sized patients, and/or having various sizes of nails to fit various types of femoral bone conditions or various types of femoral fractures, and/or further having various sizes of nails to fit various other bones. For instance, the length of the femoral nail 20 shown may be selected as needed between about 10 and 20 inches.

The distal end 26 may include a tip 30 having for instance a conical or partially conical profile. The conical profile of the tip 30 aids in inserting the nail 20 into the medullary canal. The shaft 28 may be generally of constant diameter. The proximal end 24 may include a portion of larger diameter than the shaft 28.

Figure 5:
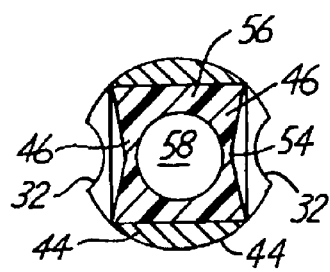
FIG. 5 is a cross-sectional view taken along lines 5—5 in FIGS. 1 and 3.
Figure 6:
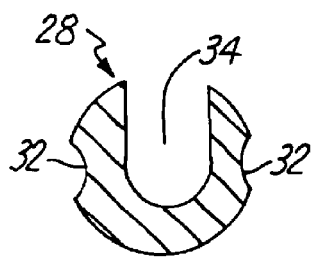
FIG. 6 is a cross-sectional view taken along lines 6—6 in FIGS. 1 and 3.

As shown in FIGS. 4–6 and known in the art, the nail 20 has an overall cross-sectional shape selected based upon the intended use. For a femoral nail 20, the cross-sectional shape may be generally circular, to match the generally circular cross-sectional shape of the medullary canal of a healthy femur. For instance, the shaft 28 may be generally formed with an outside diameter of 0.394 inches.

As best shown in FIGS. 1, 4 and 6, shallow longitudinal recesses 32 may be formed into the outside surface of the shaft 28. These longitudinal recesses 32 help to increase blood supply through the endosteum of the bone and to the fracture site during healing. Other cross-sectional shapes can be alternatively used for particular purposes or to better match the cross-sectional shape of the medullary canal of the particular bone being treated.

A cannula 34 preferably extends the length of the nail 20. The cannula 34 facilitates insertion and alignment of the nail 20 within the medullary canal. The cannula 34 may be formed at each of the ends 24, 26 by drilling along the longitudinal axis 36 of the nail 20. In the shaft 28 of the nail 20, the cannula 34 may be formed by cutting into the nail 20 from one of the sides. Alternatively, the cannula 34 may be formed by drilling longitudinally the entire length of the nail 20, which would result in a shaft 28 which encloses the cannula 34. Because the nail length is great compared with the nail width, it is generally easier to fabricate the cannula 34 by cutting laterally through the side of the shaft 28 than by drilling the length of the nail 20.

The cannula 34 receives a guide wire (not shown) during insertion of the nail 20 into the medullary canal. The guide wire has to be thick enough to provide the requisite strength and rigidity for placement into the bone, and the cannula 34 must be large enough to receive the guide wire and permit longitudinal travel of the nail 20 along the guide wire. Conversely, because a larger cannula 34 detracts from the strength of the nail 20, the cannula 34 should be as small as required for travel over the guide wire. The preferred guide wire is circular in cross-section, and as shown in FIGS. 4–6 the preferred cannula 34 generally matches this circular cross-section. For instance, the cannula 34 may be about 0.156 inches in diameter. With a shaft 28 of 0.394 inch (10 mm) diameter, this cannula 34 leaves a wall thickness for the shaft 28 of about 0.118 inches.

The preferred nail 20 includes a large radius bend 38 in the shaft 28, generally intended to match the anterior-posterior bend of a healthy femur. The bend 38 may have a large radius in relation to the length of the nail 20, such as a bend with a radius of 2 to 10 times the length of the nail 20. The curvature of the bend 38 may be applied over only a central portion of the shaft 28, leaving the proximal end 24 and distal end 26 straight. For instance, the bend 38 may be applied over a central 5 to 13 inches of the nail 20, depending on nail length.

Other than the cannula 34 being open from only one side of the shaft 28, the nail 20 is preferably symmetrical about a bisecting anterior-posterior plane. This allows the nail 20 to be used in either the right or left femur while still maintaining the bend 38 appropriate for the curvature of the femur.

The nail structure 22 is formed of a structurally strong bio-compatible material as known in the art. For instance, the nail structure 22 can be formed of a single piece of metal, with the preferred metal being titanium, such as a Ti-6AL-4V ELI titanium per ASTM F-136. For certain applications, the bone support structure may be formed of a bio-compatible ceramic or composite material of adequate strength and rigidity.

The proximal end 24 is preferably formed with one or more through-holes 40 to facilitate attachment to a proximal bone fragment. For instance, the proximal end 24 may include two holes 40 which intersect each other. As best shown in FIG. 2, each of these holes 40 preferably extends at an angle a relative to the longitudinal axis 36 of the nail structure 22, with the preferred angle a being about 46°. Both the holes 40 preferably extend at an anteversion angle β of about 15°, posteriorly (downward as shown in FIG. 1) on the proximal side and anteriorly (upward as shown in FIG. 1) on the distal side. These holes 40 allow attachment to a femoral fragment by bicortical attachment and with either antegrade fixation (i.e., through the trochanter) or reconstruction fixation (i.e., into the femoral head) as selected by the orthopedic surgeon. Alternatively or in conjunction with the through-holes 40, one or more recesses or cavities (not shown) may be provided in the proximal end 24 to permit unicortical attachment of the proximal end 24.

The proximal end 24 of the nail structure 22 may further include structure to facilitate attachment of a drilling or aligning jig (not shown) as known in the art for placement of bone fasteners relative to the nail 20. For instance, a proximal opening 42 aligned along the longitudinal axis 36 may be used to receive an end of a jig in a mating relationship. Workers skilled in the art will appreciate that numerous other structures could be equivalently used to temporarily hold the jig relative to the nail 20.

The distal end 26 of the nail structure 22 includes at least one dynamization window 44 through an external surface, with a spacer 46 in the dynamization window 44. The term "window" as used herein refers to an opening on an exterior surface of the nail 20. These windows 44 are referred to as "dynamization" windows because, when used in conjunction with a properly dimensioned bone fastener (shown in FIGS. 18–24) and with a spacer 46 formed of a bioresorbable material, the proportion of stress carried by the nail 20 relative to stress carried by the healing bone across the fracture site dynamically changes as a function of time.

If desired, a single dynamization window or cavity may be provided, which would permit only unicortical attachment of the nail 20. In the preferred embodiment, two dynamization windows 44 are provided on opposite sides of the nail 20, with each dynamization window 44 extending entirely through the side wall of the nail 20 to permit communication with the cannula 34. After removal of the guide wire from the cannula 34, the dynamization windows 44 permit bi-cortical attachment by inserting a bone fastener through the cortex on one side of the nail 20, "in" one dynamization window 44, "out" the other dynamization window 44, and through the cortex on the other side of the nail 20. While the preferred embodiment includes only one set of dynamization windows 44, additional dynamization windows may be located at other longitudinal locations of the nail 20, including the proximal end 24 and the shaft 28 as well as the distal end 26. Any additional dynamization windows may either be single dynamization windows permitting unicortical attachment or opposing sets permitting bicortical attachment. Any additional dynamization windows may either be perpendicular to the bisecting plane or at other angles through the nail 20.

In the preferred embodiment, the dynamization windows 44 are aligned on opposite sides of the nail 20 at the same longitudinal location. With this configuration, both dynamization windows 44 may be simultaneously formed by a single cutting tool advanced through the nail 20 in a direction perpendicular to the bisecting plane. Alternatively, two dynamization windows may be longitudinally (and/or radially) offset with respect to each other and still permit bicortical attachment, provided they sufficiently overlap to permit the bone fastener to simultaneously pass through both windows.

A spacer 46 is placed in each dynamization window 44. During use of the nail 20 as shown in FIGS. 18–24, a bone fastener 48 is positioned into the dynamization window 44, and the spacer 46 spaces the bone fastener 48 relative to the nail structure 22 defining the dynamization window 44. Force is transmitted between the nail structure 22 and the bone fastener 48 primarily as a compressive load on a portion of the spacer 46.

Each spacer 46 is formed of a non-metal material, and preferably of a bioresorbable material. The term "bioresorbable" as used herein refers to any biocompatible material which dissolves or degrades over time after implantation into the human body. Among others, possible bioresorbable materials include polymers and copolymers glycolic acid, lactic acid, aminocaproic acid, lactides, desoxazon, hydroxybutric acid, hydroxyvaleric acid, hydroxymethacrylate, peptides, polyesters of succinic acid and cross-linked hyaluronic acid, or even a biologically absorbable hydroxyapatite or tricalcium phosphate. The preferred bioresorbable material is a polylactic acid ("PLA"), which provides a strong material for the spacers 46. The compressibility of the PLA material shows little change over the first few weeks of implantation, but then increases linearly over the next few months until resorption to the point where the material will no longer support a load. With the preferred PLA material, full resorption will typically occur within about two to five years. If no bioresorption is desired, the non-metal material may be any other polymer commonly used in medical implants, such as a preferred non-metal non-resorbable material of ultra-high molecular weight polyethylene ("UHMWPE").

The dynamization windows 44 and the spacers 46 are shaped based on the required strength and the desired dynamization characteristics for the nail 20. In the preferred embodiment as shown in FIGS. 1 and 3, both the first and second dynamization windows 44 and spacers 46 have circular ends 50 and a rectangular central section 52, and the spacers 46 fill the dynamization windows 44 in length and width. As will be further explained with reference to FIGS. 18–24, this shape provides substantial longitudinal dynamization flexibility while still providing adequate strength for the nail 20 at the dynamization windows 44. In the 0.394 inch (10 mm) OD nail 20 and for use with 0.177 inch (4.5 mm) OD bone screws 48, each end 50 may have a circular radius of 0.124 inches, with the central section 52 being 0.345 inches in length and 0.248 inches in width, for a total dynamization window length of 0.611 inches. Similar sizes may be used in bone plates. Alternatively each spacer may not completely fill its dynamization window, such as by not being either full width or full length (which controls whether force transmitted through the spacer is in compression, in tension or in shear), or by having a central opening through each spacer.

As best shown in cross-sectional views of FIGS. 2 and 5, each spacer 46 has an exposed surface which may have a shallow groove 54 in the center. The groove 54 may provide a "V" shape to the exposed surface of the central section 52 of the spacer 46, while the exposed surface of the ends 50 of the spacer 46 may be conical. In the preferred embodiment shown, the groove 54 is about 0.04 inches (1 mm) deeper than the edges of the spacer 46. During surgical implantation of the bone fastener 48 into the nail 20, the groove 54 assists in directing the transverse guide pin/drill/bone fastener inward toward the center of the spacer 46. Workers skilled in the art will appreciate that numerous alternative surface contours may be selected for one or both spacers 46 which still provide a generally sloped surface directing the guide pin/drill/bone fastener inward toward a center of each spacer 46.

Figure 7:
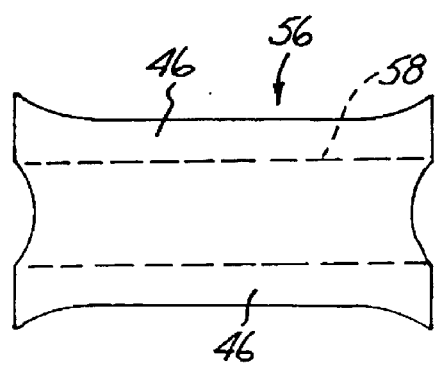
FIG. 7 is a plan view of the insert used in FIGS. 1–6.

In the preferred embodiment as best shown in FIGS. 5 and 7, the two opposing spacers 46 are formed as a single insert 56. For instance, with a 0.394 inch (10 mm) OD nail 20, the insert 56 may have an overall thickness of about 0.286 inches (7.3 mm). Alternatively, each spacer 46 may be separately formed.

A cannula 58 is formed in the insert 56 to correspond with the cannula 34 of the nail structure 22, such that the two spacers 46 are defined on opposing sides of the cannula 58. With the center of the groove 54 on the outside and the cannula 58 toward the inside, the center of each spacer 46 may be quite thin. For instance, with a cannula 58 of about 0.156 inches (3.9 mm) in diameter, the center of each spacer 46 may be only about 0.025 inches (0.6 mm) thick.

As an alternative to the groove 54, the spacer 46 may include an exposed surface which is planar. Depending upon the material of the spacer 46 and the thickness of the spacer 46 relative to the cannula 58, the center of the spacer 46 may be resiliently deflected or deformed inward under pressure. For instance, the push force placed on the spacer 46 by the guide pin, drill and/or bone fastener during insertion through the spacer 46 may cause the center of the spacer 46 to resiliently deform, such that an exposed surface which was planar as manufactured provides a sloping profile which assists in directing the guide pin/drill/bone fastener toward the center of the spacer 46.

The preferred bioresorbable material is commercially available such as in about 150 in$^3$ blocks. The insert 56 may be formed by cutting the bioresorbable material to ⅝ inch by ⅝ inch by 3 inch portions, which may then be further fabricated to the shape of the insert 56 by CNC. The cannula 58 is preferably drilled into the insert 56 prior to insertion of the insert 56 into the nail 20, although the cannula 58 may alternatively be drilled after placing the insert 56 into the nail 20, either simultaneously with or after formation of the cannula 34 through the nail structure 22.

The insert 56 may fit into the dynamization windows 44 with a press fit. The insert 56 is pressed in the nail 20 until it aligns centrally within the nail 20. Initial results have indicated that several hundreds of pounds of press force is required to press the preferred insert 56 into the windows 44 of the preferred nail structure 22. During the surgery, the insert 56 can be drilled through with a push force which is at least an order of magnitude less than the press force, and the press fit amply secures the insert 56 into the nail 20. For example, the press fit may have a pull out force of 50 pounds or more.

One way to form the press fit is to oversize the spacer 46, such as from one to several mils, in all dimensions relative to the windows 44. The press fit then creates a static compressive stress which is relatively uniform in all directions within the spacer 46. For at least some bioresorbable materials, it is believed that the amount of compressive stress changes the resorption rate and/or breakdown of the material. The amount of compressive stress and the direction of the compressive stress can thus affect the controllability and uniformity of increasing dynamization as a function of time.

During use after implantation, the intramedullary nail 20 is regularly loaded in compression and then unloaded, i.e., "longitudinal compressive cycling", such as when the healing bone supports the weight of the patient during walking. Tensile stresses and bending stresses, while occurring in the bone depending upon what the patient is doing, occur much less often and much less regularly than compressive stresses. For at least some bioresorbable materials, the typical longitudinal compressive cycling of an insert will also affect the dynamization profile. With an understanding of typical longitudinal compressive cycling of the insert, the amount of static compression and the direction of static compression created by the press fit can be selected to enhance the dynamization profile. In particular, the insert 56 can have a length which mates with the windows 44 with a first interference/clearance, and a width which mates with the windows 44 with a second, different interference/clearance. The preferred press fit places a static compression in the width direction of the insert 56, but no static compression in the length direction of the insert 56. That is, the insert 56 is oversized in the width (transverse) direction compared to the windows 44, but the length of the insert 56 matches the length of the windows 44 or leaves a slight clearance so there is no static compression stress in the longitudinal direction due to the press fit. The preferred width oversize is about 1 to 10 mils, or more preferably about 2 to 4 mils. The preferred width oversize provides a maximum static compressive stress in the transverse direction on the order of 30 to 80% of the yield stress of the preferred material of about 115 MPa, with no static compressive stress in the longitudinal direction.

There are other features which can be enhanced by the way the spacers 46 are attached into the dynamization windows 44. Various recesses or protrusions on the spacers 46 and/or in the nail structure 22 may provide a higher pull strength or facilitate a positively secured attachment of the spacers 46 to the nail structure 22. One example of this is depicted in the alternative insert 156 of FIGS. 8 and 9. In this embodiment, the insert 156 has ridges 176 extending around a portion of the insert periphery 178 which makes contact with the nail structure 22. The ridges 176 form an interference profile relative to the windows 44. The preferred ridges 176 are about 5 mils thick, extending only around the semi-cylindrical ends of the insert 156 to add about 10 mils to the longitudinal length of the insert 156.

When the insert 156 is inserted into the nail structure 22, the ridges 176 make interference contact with the windows 44 in the nail structure 22. The non-metal material of the insert 156 has a higher compressibility than the metal of the nail structure 22, and due to this interference the ridges 176 compress inward upon insertion into the nail structure 22 and place internal compression stresses on the insert 156. Because the ridges 176 occupy some but not all of the external periphery 178 of the insert 156 which contacts the nail structure, the compressive stresses caused by the ridges 176 differ locally over the exterior face of the insert 156. The width of the ridges 176 may be selected based upon the compression desired, such as a width within the range of about 5 to 50 mils. The compression of the ridges 176 thus forms one mechanism to more securely hold the spacers 46 of the insert 156 in place.

By having ridges 176 only at the longitudinal (i.e., proximal and distal) ends of the insert 156, the static compression of the ridges 176 due to the press fit occurs primarily in the longitudinal direction. The amount of static compression in both the transverse direction and the longitudinal direction can still be controlled. For example, the insert 156 can be generally oversized in the width direction, while only the ridges 176 are oversized in the longitudinal direction.

With a resorption rate that differs as a function of local compressive stress, the ridges 176 may bioresorb at a different rate than the rest of the insert structure. The location of the ridges 176 can be selected as desired, either closer to contact to bodily fluids or more removed within the nail structure 22, to further affect how the ridges 176 resorb. If desired, the ridges 176 can located and sized such that resorption of the ridges 176 is the primary mechanism for increasing dynamization of the fracture site. If desired, the nail structure 22 can be modified to include ridges (not shown) rather than including the ridges 176 on the insert 156, producing the same general effect of compressive stresses which differ locally over the exterior face of the insert.

Figure 9:
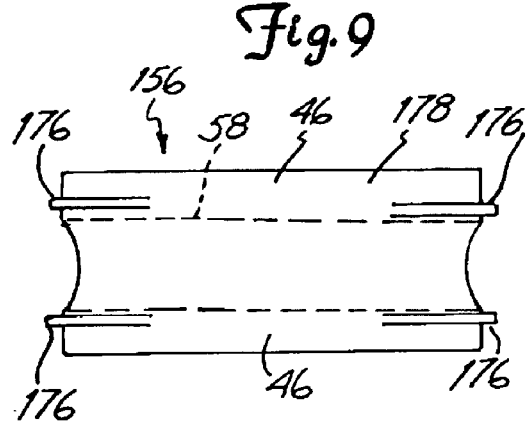
FIG. 9 is a plan view of the first alternative insert of FIG. 8.
Figure 8:
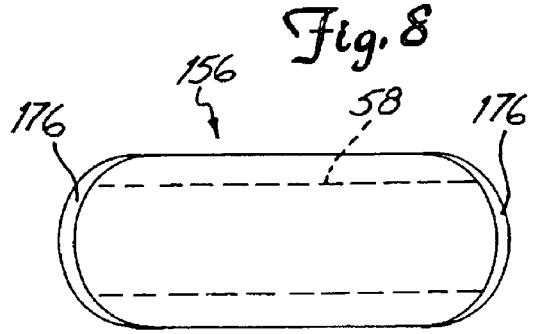
FIG. 8 is an elevational view of a first alternative insert for use with the nail structure of FIGS. 1–6.

As yet another option, the nail structure 22 can be modified to include recesses (not shown in FIGS. 8 and 9) which correspond in location to the ridges 176 on the insert 156 of FIGS. 8 and 9. If corresponding recesses are formed into an alternative nail structure, the insert 156 can be received into the alternative nail structure with a "snap fit". That is, during transverse pressing of the insert 156 into the alternative nail structure, the ridges 176 will be compressed inward until the ridges 176 snap outward into the corresponding recesses in the alternative nail structure. With such a snap fit, the ridges 176 do not contribute to the local compression stress profile of the insert 156, but rather positively lock the insert 156 into the alternative nail structure to prevent push out during transverse drilling and/or advancing the transverse bone fastener through the insert 156. Similarly to ridges 176, the nail structure 22 can be modified to include front, back, or front and back ridges or lips (not shown) which would prevent push-through and/or pull-out of the insert 56, 156 from the windows 44.

Figure 10:
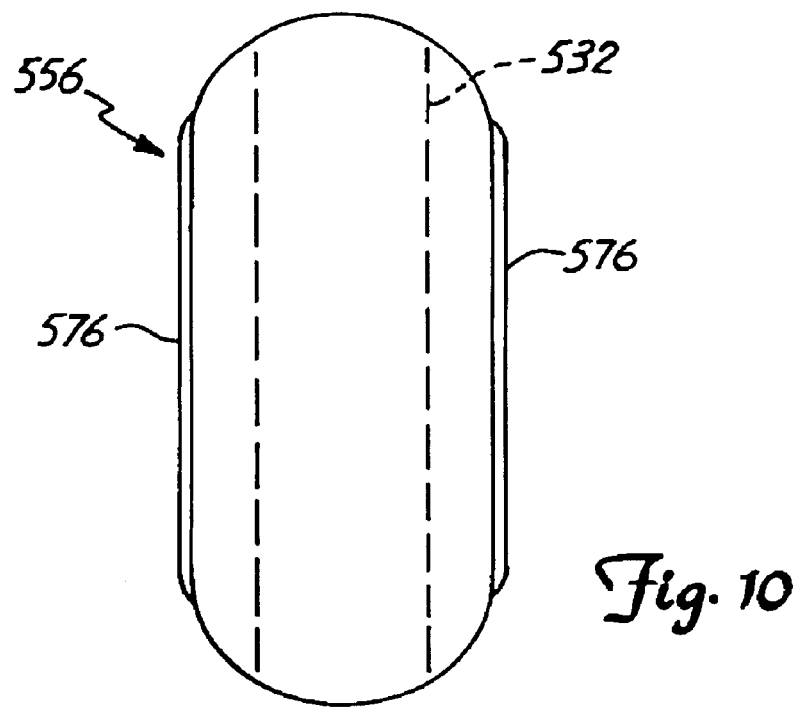
FIG. 10 is an elevational view of a snap fit alternative insert.
Figure 11:
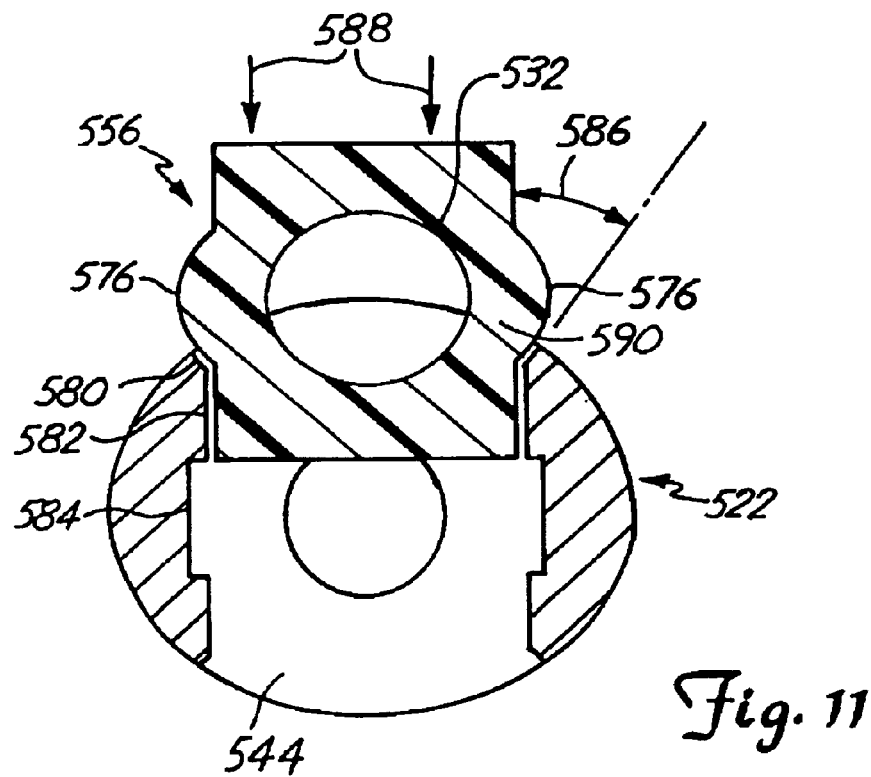
FIG. 11 is a cross-sectional plan view of the snap fit alternative insert of FIG. 10, shown during insertion into an alternative nail structure.

A "snap fit" example is depicted in the alternative insert 556 of FIGS. 10 and 11. In this embodiment, the insert 556 has bump ridges 576 extending around a portion of the insert periphery 578 which makes contact with the nail structure 522. As best shown in FIG. 11, the window 544 includes a mouth portion 580, a neck portion 582, and a receiving notch 584. The bump ridges 576 form an interference profile relative to the neck portion 582. For instance, other than the bump ridges 576, the preferred insert 556 has a width which is nominally 2 mils narrower than the neck portion 582, permitting a slight clearance during insertion of the insert 556 into the window 544. The width of the bump ridges 576 may be selected based upon the desired push force to insert the insert 556 into the nail 522, and based upon the desired amount to interference to prevent the insert 556 from being undesirably removed from the nail 522, such as a bump ridge width within the range of about 5 to 50 mils. The preferred bump ridges 576 are about 20 mils wider than the rest of the insert 556, providing an interference relative to the neck portion 582 of about 9 mils per side. The preferred bump ridges 576 are circular in profile, concentric with the cannula 534. The preferred mouth portion 580 widens slightly relative to the neck portion 582, such as at an angle 586 of about 30°.

Insertion of the insert 556 into the nail structure 522 is simple and straight-forward. First, the insert 556 is positioned and oriented immediately adjacent the window 544. Positioning of the insert 556 can be performed by hand or with a pliers, tweezers or similar grasping tool. The widening of the mouth portion 580 assists in aligning the insert 556 relative to the window 544. Once aligned with the axis of the window 544, the insert 556 can be freely advanced into the nail structure 522 until the bump ridges 576 contact the mouth portion 580, i.e., to the position shown in FIG. 11. In this position, the bump ridges 576 begin to make interference contact with the mouth portion 580. The bump ridges 576 thus represent a trailing portion of the surface of the insert 556 which makes contact with the nail structure 522 upon insertion. In contrast to the rest of the contact surface of the insert 556 which extends parallel to the insertion axis, the bump ridges 576 extend at angles relative to the insertion axis.

The preferred bump ridges 576 are provided with a radius and curvature which roughly corresponds to the angle of the mouth portion 580. That is, the preferred bump ridges 576 have about a 60° arc portion which extends beyond the rectangular profile (in cross-section) of the rest of the contact surface of the insert 556, with about a 150° intersection or corner at the leading side of each bump ridge 576 and about a 150° intersection or corner at the trailing side of each bump ridge 576. The non-metal material of the insert 556 has a higher compressibility than the nail structure 522, and, when the insert 556 is forced into the nail structure 522 as shown by arrows 588, the angle 586 of the mouth portion 580 compresses the bump ridges 576 inward. Because the bump ridges 576 are concentric with the cannula 532, the sidewall 590 adjacent the bump ridge 576 can further accept the interference by deflecting inward into the cannula 532. In the preferred embodiment, this sidewall 590 has a wall thickness of about 0.04 inches.

The insert 556 is pushed further into the nail structure 522, until the bump ridges 576 snap outward into the receiving notches 584. In the preferred embodiment, the receiving notches 584 have a cornered profile. The cornered profile does not compress the bump ridges 576 nearly as efficiently as the angle 586 of the mouth portion 580. Thus, once the insert 556 is snapped into place within the nail structure 522, the push force required to remove the insert 556 from the nail structure 522 may be several times the push force which was initially required to place in the insert 556 into the nail structure 522. In the preferred embodiment, the receiving notches 584 still provide a slight interference with the insert 556, such as 2–3 mils interference. This slight interference restricts movement of the insert 556 relative to the nail structure 522, despite the slight clearance between the insert 556 and the neck portions 582.

The insert 556 and the nail structure 522 shown are symmetrical about a plane perpendicular to the push or insertion axis. Thus, it is equally possible to press the insert in from either side of the nail structure. Similarly, the insert may be pushed into place with either side pushed in first (i.e., orienting the insert 556 right-side-up as shown in FIG. 11 or upside-down does not matter). If desired, the bump ridges 576, the receiving notches 584 or both may be formed non-symmetrically. For instance, if desired the bump ridges 576 may be formed with a squared back end, of a shape and size to mate like a barb with the corner of the receiving notches 584. By forming a barb-type interference between the bump ridges 576 and the receiving notches 584, an even higher "pull out" force can be obtained with a lower "push in" force. Workers skilled in the art will thus appreciate that many other shapes can be used to provide a snap fit to the insert.

Figure 12:
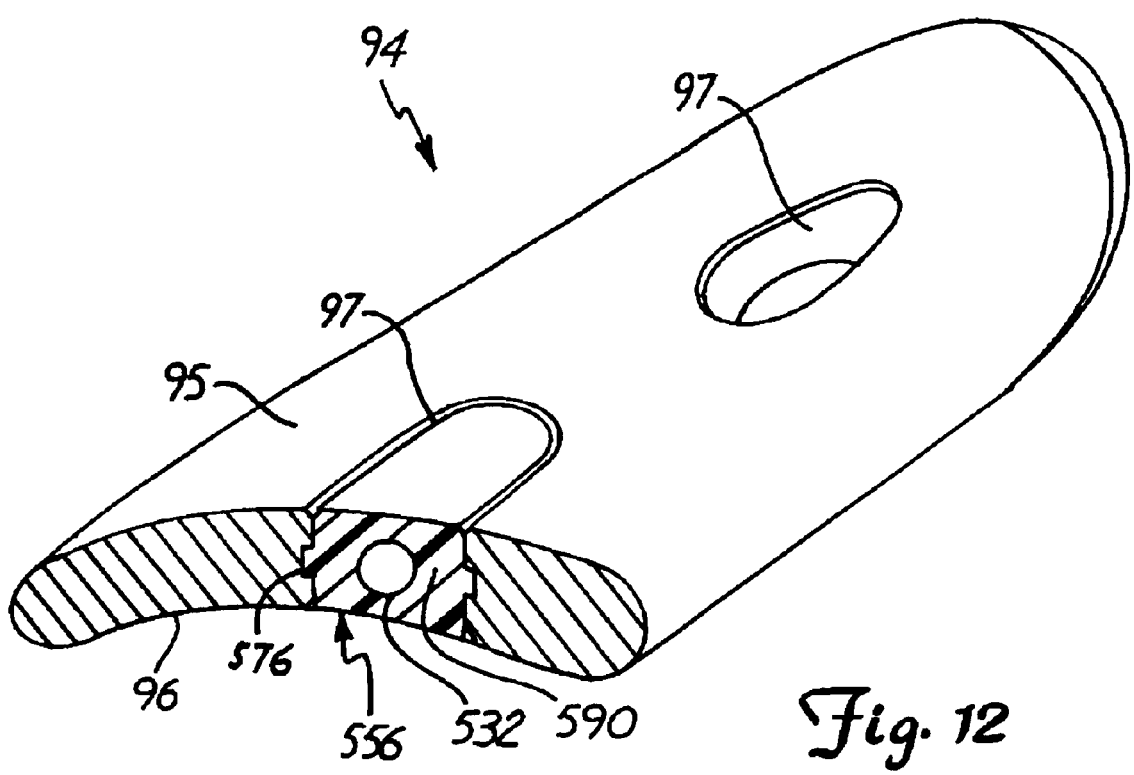
FIG. 12 is a perspective view in partial cross-section showing use of the snap fit alternative insert of FIGS. 10 and 11 as used in a bone plate.

In addition to the nail 22, 522 shown in FIGS. 1–11 and 13–24, the present invention also has a wide range of applicability in other bone support implant devices, such as in a bone plate 94 as shown particularly in FIG. 12. Even though the present invention is described largely with reference to the intramedullary nail structure 22, 522 much of the description applicable to the intramedulary nail structure 22, 522 of FIGS. 1–11 and 13–24 is equally applicable to bone plates or other bone support implant devices.

The bone plate 94 shown in FIG. 12 has a top surface 95 and a bone-contact surface 96. The bone plate 94 has an overall cross-sectional shape selected as known in the art based upon the intended use of the bone plate 94. A plurality of through-holes 97 extend through the bone plate 94. The holes 97 are provided to receive bone fasteners to secure the bone plate 94 to portions of the bone (not shown). If desired, the holes 96 may have a surface profile as known in the art which interacts with the head of a bone fastener to apply either compressive or tensile stress across a fracture site.

In a preferred embodiment, each of the holes 97 are similarly shaped. A plurality of inserts 556 are included in a bone support kit. Based upon the fracture site and/or the desired treatment modality, the surgeon then selects which holes 97 should be filled with inserts 556 and which inserts 556 should be used. In particular, one or more holes 97 may be left open, while one or more other holes 97 are filled with inserts 556. The use of bone fasteners in insert-filled holes allows dynamization across the fracture site as desired by the surgeon. The use of bone fasteners properly positioned in open holes 96 may prevent dynamization until those bone fasteners are subsequently removed.

Bone plates are utilized on the surface of the bone, with bone fasteners which extend through the bone plate into the bone. In contrast to nails, i.e., because bone fasteners when used with bone plates do not extend through the bone prior to reaching the bone support implant, issues previously discussed with regard to unicortical or bicortical attachment are less significant with regard to bone plates. The bone plate 94 is attached with bone fasteners inserted through the holes 97 in the bone plate 94 and secured into bone. The holes 97 in the bone plate 94 will accordingly always be through-holes, not cavities.

Because bone plates are utilized on the surface of the bone, use of a guide wire within a longitudinally extending cannula is generally unnecessary for bone plates. However, the preferred insert used with a bone plate 94 may still retain a longitudinally extending cannula 532, even if no corresponding cannula is machined into the plate structure 94. As when used with a cannulated nail 20, the central cannula 532 in the insert 556 places the bump ridges 576 on a relatively thin sidewall 590, which can be bent/compressed inward during insertion of the insert 556 into the bone plate 94.

Attachment of the insert(s) into the dynamization window(s) does not have to be performed as a manufacturing step. Alternatively, the surgeon may attach the inserts into the dynamization windows as a preparatory step during surgery, and the bone support implant and inserts may be appropriately modified to facilitate placement of the insert(s) into the dynamization window(s) by the surgeon. As used herein, the term "surgeon" includes any treating physician or any treatment professional under the direction of a surgeon or other treating physician. For instance, the insert(s) and dynamization windows may have a smaller amount of interference to enable the surgeon the press the insert(s) into the bone support implant by hand. Alternatively, the surgeon may be provided with a mechanical press to facilitate pressing the insert(s) into the bone support implant. If the insert has an interference profile so as to be received in the bone support implant with a snap fit, the surgeon obtains the additional comfort of knowing the insert is properly positioned when the insert snaps into place.

If desired, a lubricant may be utilized to facilitate the press fit or snap fit. The lubricant used may be volatile, so the insert becomes tightly secured into the bone support implant after the lubricant evaporates. As another alternative, the insert and the dynamization windows may be sized with a slight clearance and be adhesively secured. Any lubricant or adhesive should be biocompatible so as to not create complications in the healing process.

Attachment of the insert into the dynamization windows by the surgeon allows several further advantages. For instance, a single bone support implant may be provided as part of a kit which includes a plurality of inserts having different properties. The different inserts provided may have different mechanical properties, such as different hardnesses, different rates of absorption, etc., allowing the surgeon the flexibility to match the insert used with the particular healing modality desired by the surgeon. One or more of the inserts in the kit may be bioresorbable, while one or more other inserts in the kit are not. Thus, the surgeon may select whether dynamization occurs at all. One preferred kit includes a first insert which starts dynamization at two to four weeks after implantation and fully dynamizes after ten to twelve weeks, a second insert which starts dynamization at eight to ten weeks and fully dynamizes after about sixteen weeks, and a third insert which does not bioresorb. Each of the differing inserts in the kit is preferably marked or color-coded so the surgeon can quickly identify which insert has the desired mechanical or chemical treatment properties.

The inserts may also include one or more active agents to promote effective healing. For instance, the non-metal material of the inserts may include one or more antibiotics such as gentamicin, methicillin, penicillin, etc. The non-metal material of the insert may also include other active agents, such a one or more of a transforming growth factor-beta 1, a recombinant human bone morphogenetic protein-2, etc. If provided as part of a kit, different inserts may be provided each with a different active agent or a different amount of active agent, so the surgeon can select the type and amount of active agent used for the particular surgery.

Additional flexibility is provided if the bone support implant has multiple sets of dynamization windows 44. If the bone support implant has multiple sets of dynamization windows 44, the surgeon may elect to press inserts into less than all of the windows 44, or to press inserts having different physical or mechanical properties into the various dynamization windows 44.

Another advantage of attachment of the insert into the dynamization windows 44 by the surgeon is that the insert may be handled in a different environment from the nail structure 22. For instance, the insert may be maintained in a particular thermal condition (e.g., refrigerated or frozen), or in a sealed container (e.g., sealed from air, sealed from humidity, etc.) until immediately prior to insertion into the dynamization windows 44 and immediately prior to implantation into the fractured bone. The controlled environment of the insert may have beneficial results in physical properties (e.g., preventing dissipation or dilution of an active agent, etc.) or in mechanical properties (e.g., increased hardness, different size due to thermal expansion, etc.) of the insert upon implantation.

Figure 13:
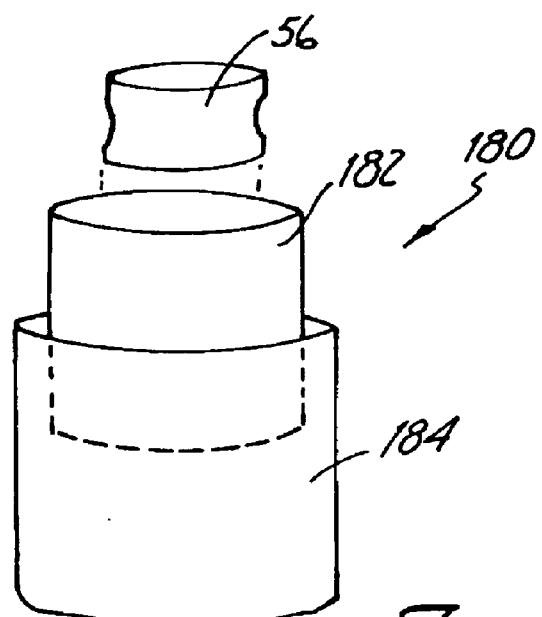
FIG. 13 is an exploded perspective view depicting packaging of the insert of FIGS. 1–7 into a preferred sealed container.

FIG. 13 depicts one preferred container 180 during assembly to be sealed about the insert 56. The preferred container 180 is a double layer pouch. An inner pouch 182 is sealed around the insert 56 and formed such as of PET, aluminum foil and polyethylene or polypropylene. An outer pouch 184 is sealed around the inner pouch 182 and formed such as of TYVEK spun bond polyethylene, paper, polyester and/or polyethylene. The sealed container 180 is specially designed to maintain sterility of the insert 56 until use and to increase the shelf-life of the insert 56. In particular, the sealed container 180 substantially prevents the insert 56 from contacting germs, air, and moisture or humidity. The foil and/or paper shields the insert 56 from light. The foil and/or paper can also include printing such as identifying the insert 56 and instructional information. Depending upon the material selected for the insert 56, water absorption from humidity, oxidation, or light degradation of the polymer may affect the dynamization profile for the insert 56. In that the Insert 56 should have a consistent dynamization profile regardless of the length of time the insert 56 has sat on the shelf prior to placement into the nail structure 22 and implantation, the sealed container 180 is important for shelf-life. For instance, the container 180 may be flushed with nitrogen upon sealing, such that the insert 56 is retained in a nitrogen environment for prolonged shelf-life. The double-layer pouch 180 facilitates use of the insert 56 in a sterile operating theater.

Prior to sealing the insert 56 in the container 180, the insert 56 should be sterilized. One method of sterilization is through Cobalt 60 Gamma irradiation, such as at about 2.5 to 4 Mrad or a dose of about 25 to 40 kGy. Gamma irradiation sterilization changes the morphology of the preferred bioresorbable material, such as through chain-scission or cross-linking, which causes some reduction of average molecular weight. Of particular importance, the gamma irradiation increases the rate of degradation of the preferred bioresorbable material, and thus the effects of the gamma irradiation must be taken into account in selecting the insert material for a desired dynamization profile. A second method of sterilization is through ethylene oxide gas sterilization, which is believed not to significantly affect the dynamization profile. A third method of sterilization is through gas plasma sterilization, which is believed to result in a slower dynamization profile on the preferred material than gamma irradiation. Gas plasma sterilization is also appropriate for inserts of non-resorbable materials such as polyethylene (low molecular weight or UHMWPE). After sterilization and prior to sealing in the container 180, the insert may be dried such as through vacuum drying.

Figure 14:
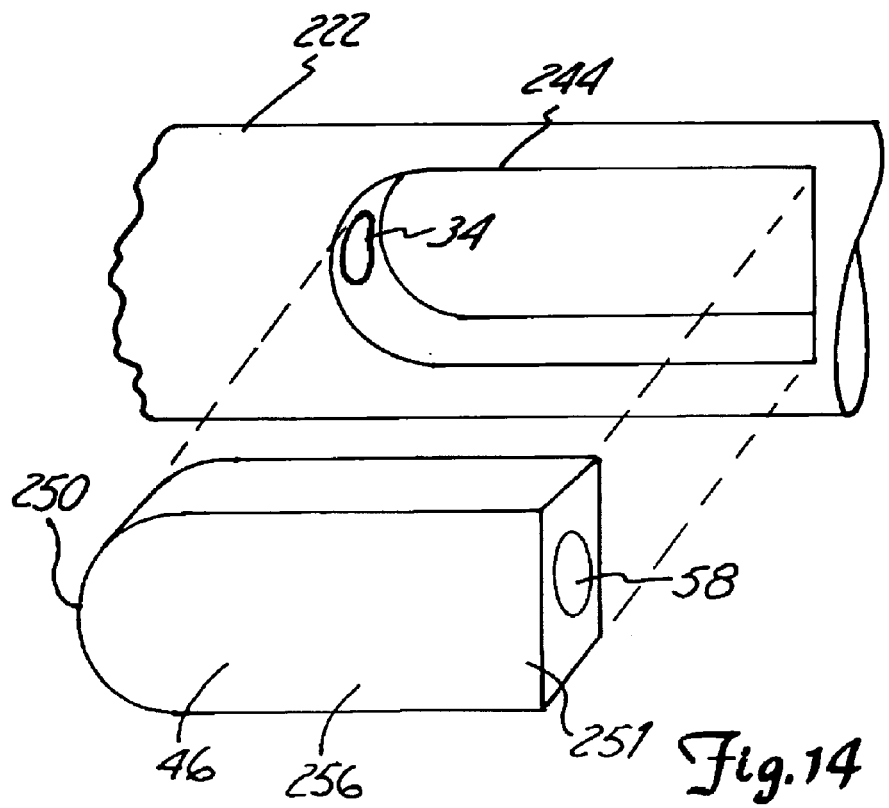
FIG. 14 is a plan view of third alternative insert used in a corresponding nail structure.

FIG. 14 shows a third alternative insert 256 positioned for insertion in a corresponding nail structure 222. As shown, this insert 256 and its window 244 have differing shapes between distal end 250 and proximal end 251. The proximal end 251 of the insert 256 transmits compressive loads to the nail structure 222, whereas the distal end 250 of the insert 256 transmits tensile loads to the nail structure 222. The difference between shapes at the proximal and distal ends 251, 250 is particularly appropriate for weight bearing bones such as the femur because such weight bearing bones are much more often loaded in compression than in tension. The squared off proximal end 251 of the insert 256 transmits compressive stress across a wider surface area than the semi-cylindrical proximal end 50 of FIGS. 1–13. The squared off proximal end 251 of the insert 256 also has a more uniform compressive stress load across its width, rather than concentrating the compressive stress load along the centerline of the insert 56. The third alternative insert 256 is also applicable for use with bone plates or other bone support implants.

Figure 15:
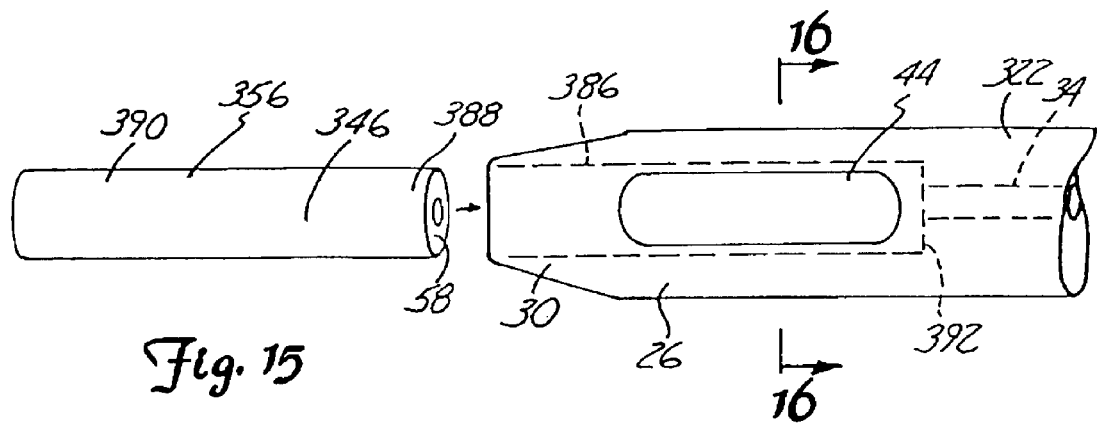
FIG. 15 is an exploded plan view of a fourth alternative insert for axial insertion into a corresponding nail structure.
Figure 16:
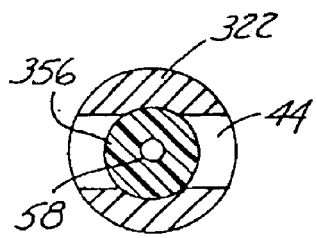
FIG. 16 is a cross-sectional view taken along line 15—15 in FIG. 14 after assembly.

Further along the lines that the spacer or insert, for certain bones, will rarely transmit tensile stresses, FIGS. 15 and 16 show an axial insert 356. FIG. 15 shows the axial insert 356 aligned for axial insertion into a corresponding insert reception recess 386 in a distal end 26 of a nail structure 322. During assembly, the axial insert 356 is advanced axially into the insert reception recess 386. Assembly may be performed either as a manufacturing step or by the surgeon immediately prior to implantation. Depending upon which bones are being treated and the desired treatment modality, the axial insert insert 356 may also be used with bone plates or other bone support implants.

With axial insertion, the axial insert 356 can be sized significantly larger and/or longer than the window 44, so there is substantially no possibility of a transverse push-out of the axial insert 356 such as due to the drill force. For example, the axial insert 356 has proximal and distal extensions 388, 390 around a spacer portion 346. When the axial insert 356 is positioned in the insert reception recess 386, only the spacer portion 346 is visible in the windows 44. When the axial insert 356 is positioned in the insert reception recess 386, the proximal and distal extensions 388, 390 project beyond the proximal and distal ends of the windows 44. For instance, each of the proximal and distal extensions 388, 390 may be 0.05 inches or longer in length. In the preferred axial insert 356 shown in FIG. 15, the axial insert 356 is about 0.9 inches in length, while the windows 44 are only about 0.55 inches in length. When fully inserted, the proximal extension 388 extends proximally about 0.05 inches past the proximal end of the windows 44, and the distal extension 390 extends distally to the end of the nail structure 322, about 0.25 inches beyond the distal end of the windows 44.

The proximal end 388 of the axial insert 356 abuts against the proximal end 392 of the receiving opening 386 in the nail structure 322 to transmit compressive loads to the nail structure 322. Thus, in a nail structure 322 with a cannula 34, the axial insert 356 should have transverse dimensions which are significantly greater than the diameter of the cannula 34, to transmit the compressive stress across sufficient surface area. The axial insert 356 and the corresponding receiving opening 386 in the distal end 26 of the nail structure 322 may be formed in simple cylindrical shapes. For instance, in a nail structure 322 with a 0.12 inch diameter cannula 34, the axial insert 356 may have about a 0.25 inch diameter. This leaves a surface area of $(0.25^2–0.12^2)\pi/4$ square inches to support the compressive load placed upon the fractured bone. A 0.12 inch diameter cannula 58 also extends through the axial insert 356, so the guide wire (not shown) can be used in the traditional manner.

As mentioned previously, intramedullary nails transmit tensile forces much less frequently than compressive forces, and the tensile forces transmitted are typically much smaller in magnitude. Still, the axial insert 356 should have some interference which will prevent the axial insert 356 from freely moving out of the corresponding receiving opening 386 in the distal direction if a tensile force is being transmitted. For example, the axial insert 356 may be formed with a 2 to 10 mil interference in the receiving opening 386, and retained with a press fit. The press fit will only place a static compressive load on the axial insert 356 in the transverse direction, and thus will have only minor impact on the degradation rate of a bioresorbable material for the axial insert 356.

If desired, the axial insert 356 may be formed with a spacer portion 346 which is slightly larger in diameter than the distal extension 390. For instance, the distal extension 390 may be formed with a diameter which matches the diameter of the receiving opening 386, and the spacer portions 346 of the axial insert 356 may be formed having a diameter which is 2 to 10 mils larger and in the shape of the windows 44. With such a configuration, axial insertion of the axial insert 356 into the receiving opening 386 is only achieved with a press force which compresses the spacer portion 346 of the axial insert 356 radially inward. Then, when fully inserted into the nail structure 322, the spacer portion 346 uncompresses and springs radially outward into the windows 44, locking the axial insert 356 from sliding distally in the nail structure 322.

Figure 17:
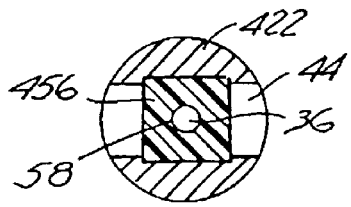
FIG. 17 is a cross-sectional view of a fifth alternative insert axially inserted into a corresponding nail structure.

FIG. 17 shows an axial insert 456 which has a non-circular shape in transverse cross-section. With a square cross-sectional shape, the axial insert 456 better supports twisting stress on the intramedullary nail 422. That is, in contrast to the cylindrical insert 356 of FIGS. 15 and 16, the square cross-sectional shape prevents the axial insert 456 from rotating about the longitudinal axis 36. Other shapes which are non-circular in transverse cross-section can be similarly used.

As shown in FIGS. 1–3, the distal end 26 of the preferred nail 20 preferably includes a non-dynamic through-hole 60. The through-hole 60 has an axis 62 which is preferably perpendicular to the anterior-posterior plane and intersecting the longitudinal axis 36 of the nail 20. The through-hole 60 defines a first window 64 into the cannula 34 and a second window 64 out of the cannula 34 at the opposite side of the nail 20. Each window 64 may be circular in cross-section, and both windows 64 may be defined with a single drilling operation. The size and shape of the windows 64 are selected based on the intended bone fasteners to be used. For instance, both windows 64 may be circular with a 0.217 inch diameter. For bi-cortical attachment of the distal end 26 of the nail structure 22 using the through-hole 60, a bone fastener 48 is advanced through the through-hole 60, i.e., through both windows 64. While the preferred embodiment includes only one set of non-dynamization windows 64, additional non-dynamization windows 64 may be located at other longitudinal locations of the nail 20, including the proximal end 24 and the shaft 28 as well as the distal end 26. Any additional non-dynamization windows may either be single windows permitting unicortical attachment or opposing sets permitting bicortical attachment. Any additional non-dynamization windows may either be perpendicular to the bisecting plane or at other angles through the nail 20.

Similarly, non-dynamization holes may be provided through the bone plate or other bone support implant.

The bone fasteners 48 used with the bone support implant 20 may be for instance bone pins or bone screws, sized and shaped as appropriate for the site of implantation. Each bone fastener 48 may be directly implanted into the cortex, or a hole may be drilled or otherwise opened in the cortex prior to placement of the bone fastener 48. The bone pin or bone screw may be solid, or may be cannulated such as for implantation over a guide pin. In the preferred embodiment, the distal through-hole 60 is sized to receive 0.177 inch (4.5 mm) outside diameter bone screws, and the dynamization windows 44 and spacers 46 are sized appropriately for 0.177 inch (4.5 mm) outside diameter bone screws. The proximal through-holes 40 as preferably sized appropriately for 0.256 inch (6.5 mm) outside diameter bone screws. Other types of bone fasteners may be alternatively used at the option of the orthopedic surgeon.

Figure 19:
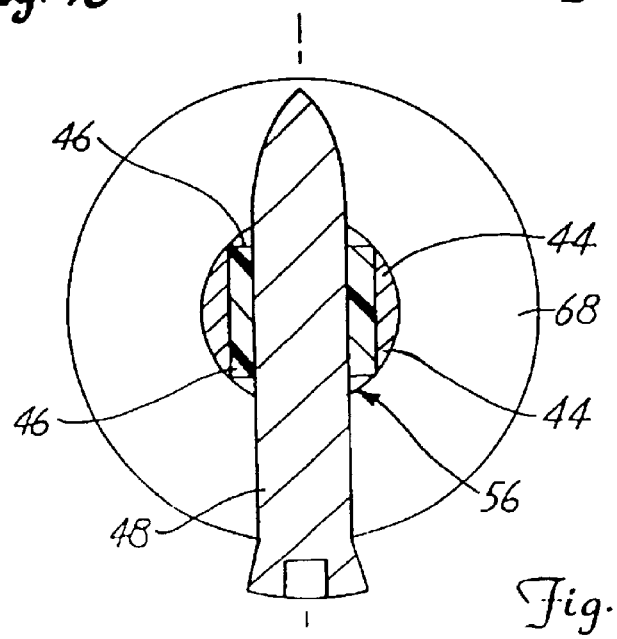
FIG. 19 is a cross-sectional view taken along lines 18—18 in FIG. 17.

FIGS. 18–24 show various attachment configurations for the nail 20 of the present invention. Though not shown in separate figures, the various attachment configurations shown in FIGS. 18–24 are also generally applicable for bone plates. FIGS. 18 and 19 show a bicortical attachment with a single bone screw 48 positioned at the distal end of the two dynamization windows 44, which can be characterized as an "initial dynamic" locking position. Attached in this position, the nail 20 provides only compressive dynamization across the fracture site 66, as follows. The bioresorbable spacer 46 can be thought of as a compression spring with a time-varying spring constant, positioned within a substantially incompressible nail structure 22. In the attachment shown in FIGS. 18 and 19, substantially the entire length of the "spring" is on the proximal side of the bone fastener 48. Very little force is transmitted through the nail 20 until the bone is loaded. When the fractured bone is loaded in compression, the compressive load is carried across the fracture site 66 by the nail shaft 28 and then through the proximal length of the spacer 46, and then to the bone fastener 48 and distal fragment 68. Initially on implantation, the bioresorbable spacer 46 is very rigid and hard, and substantially incompressible like the nail structure 22. The nail 20 will carry substantially all of the compressive force, and none of the compressive force will be carried across the fracture site 66.

After the bone begins healing, such as after several weeks, the bioresorbable material begins to deteriorate. This increases the compressibility (lowers the spring constant) of the bioresorbable material in the dynamization window 44. In this condition, when a compressive stress is placed across the fracture site 66, the proximal side of the spacer 46 will compress slightly under the load. Because of this slight compression, significant amounts of the compressive stress will be carried by the healing bone as well as by the nail 20.

As the bioresorable material further deteriorates, the proportion of stress carried by the nail 20 relative to stress carried by the healing bone continues to decrease. The healing bone continues to be dynamized, until substantially all compressive stresses placed on the bone are carried across the fracture site 66 rather than by the nail 20.

Most of the stresses carried by the bone are compressive stresses rather than tensile stresses. Nonetheless, in contrast to the compressive dynamization, consider the path of tensile stress placed on the bone when the nail 20 is attached as shown in FIGS. 18 and 19. When the bone is loaded in tension, the tensile stress is carried across the fracture site 66 by the nail shaft 28 and then around to the distal side of the dynamization window 44 by the nail structure 22, then transferred as a compressive stress through only a small distal length of the spacer 46, and then to the bone fastener 48 and distal fragment 68. Because the bone fastener 48 is quite close to the distal end of the dynamization window 44, there is a very short length of bioresorbable material to undergo compression, and there is very little give in the short distal length of bioresorbable material regardless of the amount of deterioration. Tensile stresses placed across the fracture site 66 are almost entirely borne by the nail 20, regardless of deterioration of the bioresorbable spacer 46.

FIG. 20 shows an alternative attachment of the nail 20, which can be either a "static" locking position or a "delayed dynamic" locking position depending upon screw removal. In this static locking position, the nail 20 is attached with a first bone screw 48 through the open through-hole 60 and a second bone screw 48 through a distal end of the dynamization windows 44. The two screw attachment helps further secure the distal fragment 68 to the nail 20, and particularly helps to prevent any rotational movement or "toggling" of the distal fragment 68 which might otherwise occur about a single screw. Toggling of the distal fragment 68 may particularly be a problem if the distal end 26 of the nail 20 does not fit securely and tightly within the medullary canal of the distal fragment 68.

With two screw attachments and particularly with the screw 48 through the open through-hole 60, there is very little dynamization which is initially seen by the fracture. However, an intermittent operation may be performed after initial healing of the fracture in which the bone screw 48 through the open though-hole 60 is removed, resulting in the delayed dynamic configuration. With a single screw attachment through the distal end of the dynamization windows 44, compressive dynamization of the fracture will be achieved after the intermittent operation.

Figure 21:
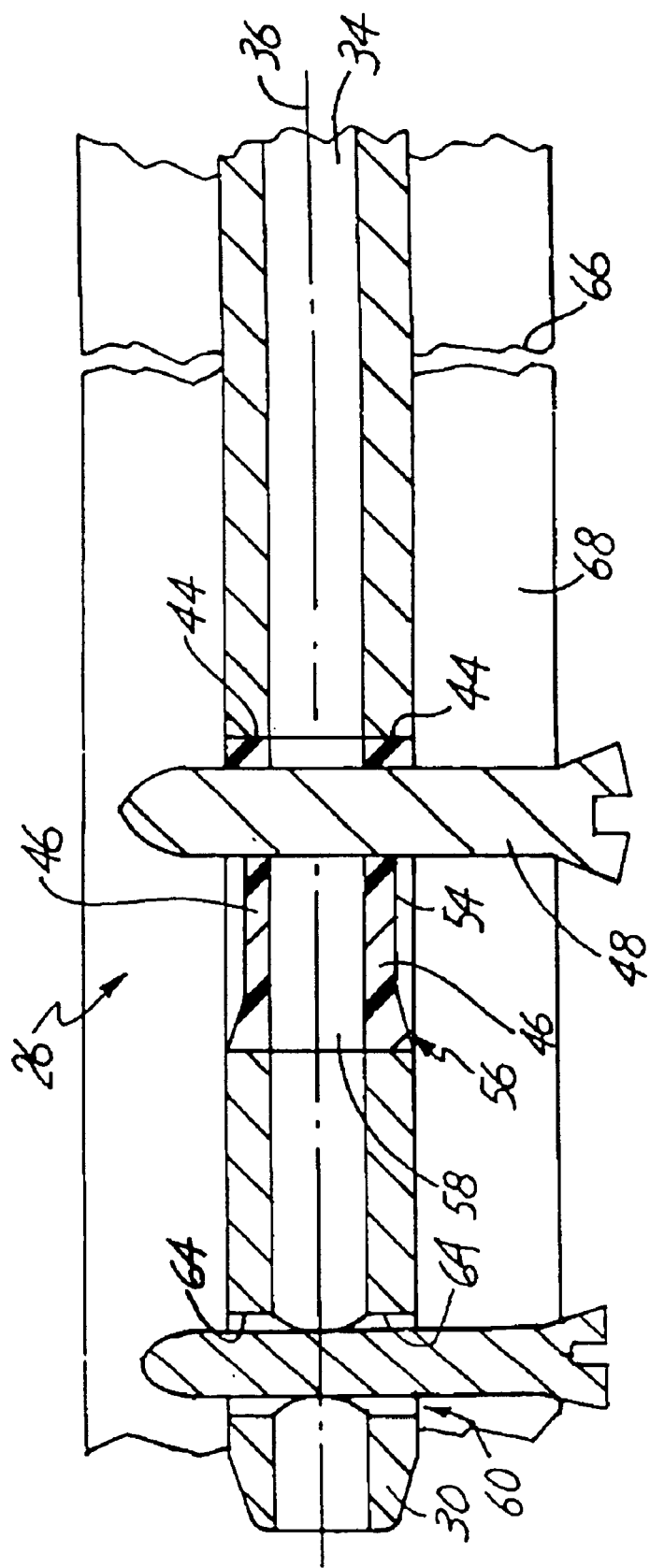
FIG. 21 is a cross-sectional view of a distal end of the nail of FIGS. 1–6 in a third type of attachment to a bone.

If a completely static attachment is desired, the recommended positioning of bone screws 48 includes a first screw 48 through the open through-hole 60 and a second bone screw 48 through a proximal end of the dynamization windows 44 as shown in FIG. 21. This positioning allows maximum separation between the bone screws 48 for toggle prevention and maximum strength. For each of the initial dynamic, the delayed dynamic and the completely static attachments, the surgeon can further adjust bone screw positioning as necessary for the condition of the bone.

In an alternative nail design (not shown) having two distal sets of dynamization windows 44, toggling of the distal fragment 68 will be prevented by a two screw attachment while full dynamization can be achieved without removal of either screw.

Many middle grounds or intermediate longitudinal locations can also be selected by the surgeon for placement of the bone screw 48 through the dynamization windows 44. By selecting the longitudinal location of the bone screw 48 through the dynamization windows 44, the surgeon can select the proportion of compressive dynamization and tensile dynamization seen at the fracture site 66.

The dynamization windows 44 are significantly longer than the width of the intended bone fastener 48. Because of this, while the exact longitudinal location of the bone fastener 48 is important for the desired dynamization, the exact longitudinal location is not critical to use of the nail 20. Minor longitudinal displacement errors of the bone fastener 48 will not prevent the bone fastener 48 from being advanced through the nail 20. The preferred nail structure 22 permits longitudinal displacement of the preferred bone fastener 48 up to a maximum of 0.434 inches while still receiving the bone fastener 48 through both windows 44. This large range of longitudinal location of the bone fastener 48 relative to the dynamization windows 44 not only provides permissible error for the surgeon, but also allows the surgeon flexibility in placement of the bone fasteners 48 relative to the fracture and relative to changes in bone condition at different longitudinal locations.

FIGS. 22–24 further show how the present invention provides flexibility in locating the bone fastener(s) 48 relative to the intramedullary nail 20 and also in providing for a range of error in locating the bone fastener(s) 48 relative to the nail 20. These benefits are achieved due to the different mechanical properties (such as hardness) of the non-metal material of the spacers 46, regardless of whether the non-metal material chosen is bioresorbable.

The longitudinal length of the two windows 44 with respect to each other allows for a significant longitudinal angulation γ of the bone screw 48 relative to the nail 20, such as up to about 45° as shown in FIG. 22. Three factors may result in the longitudinal angulation γ of the bone screw 48. Firstly, the location of the bone fastener 48 shown in FIG. 22 may result in a bending dynamization of the fracture site 66. The bone fastener 48 contacts the nail 20 at a proximal end 70 of one dynamization window 44 and at a distal end 72 of the other dynamization window 44. Tensile loads are transmitted through the distal end 72 contact without dynamization, and compressive loads are transmitted through the proximal end 70 contact without dynamization. However, bending stress such as that created by placing a clockwise (in FIG. 22) moment on the distal fragment 68 may allow dynamization. The extent of bending dynamization of the fracture site 66 depends on how secure the distal end 26 is in the medullary canal of the distal fragment 68. A loose fit of the distal end 26 in the distal fragment 68 will allow some rotational play, and the compressibility of the spacer material will govern how much bending stress is transferred through the fracture. Conversely, a tight fit of the distal end 26 in the distal fragment 68 will prevent any clockwise bending dynamization, as the distal fragment 68 cannot rotate relative to the nail 20 due to the tight fit. A loose fit of the distal end 26 in the distal fragment 68 may result either from the condition of the original bone or due to widening the medullary canal during surgery relative to the diameter of the nail 20. If the surgeon wishes clockwise bending dynamization to occur, first a loose fit must be obtained, and then the bone fastener 48 is placed through the dynamization windows 44 as shown in FIG. 22. Through proper longitudinal angulation γ of the bone fastener 48, the structure of the preferred nail 20 thus allows the surgeon to select whether, how much, and in which direction bending dynamization occurs.

A second reason for longitudinal angulation γ of the bone fastener 48 is based on the condition of the fracture. With longitudinal angulation γ of the bone fastener 48, the bone fastener 48 extends through one side of the cortex at a position longitudinally offset from the location the bone fastener 48 extends through the other side of the cortex. The surgeon may determine that significant longitudinal angulation γ is necessary for best securement of the bone fastener 48 relative to the fracture location(s).

A third reason for longitudinal angulation γ of the bone fastener 48 is merely due to longitudinal angular misalignment of the bone fastener 48. The axis of the bone fastener 48 may be angularly misaligned relative to its desired position. The structure of the preferred nail 20 permits longitudinal angular misalignment of the bone fastener 48 while still receiving the bone fastener 48 through both windows 44.

As best shown in FIG. 23, the width of the two windows 44 is preferably greater than the width of the bone fastener 48. This difference in width permits some transverse displacement 74 of the bone screw 48 with respect to the longitudinal axis 36 of the nail 20, either by error or as intended by the surgeon. The structure of the preferred nail 20 in conjunction with the preferred bone fastener 48 permits a transverse displacement 74 up to a maximum of 0.071 inches. Because the spacer material is drilled in-situ or the bone fastener 48 used opens its own hole through the spacer 46, the spacer 46 holds the bone fastener 48 securely with respect to the nail 20 anywhere within the dynamization windows 44, at least until resorption of the spacer 46 becomes significant.

As best shown in FIG. 24, because the width of the windows 44 is greater than the width of the bone screw 48, some amount of transverse angulation δ is also permitted. Similar to transverse displacement 74, this transverse angulation δ may either be the result of error or be intended by the surgeon. The structure of the preferred nail 20 permits a transverse angulation δ with the preferred bone fastener 48 up to a maximum of about 11° from the axis of the dynamization windows 44.

The preferred PLA material for the spacers 46 and the preferred shape of the spacers 46 provide very useful general purpose dynamization characteristics based on currently known information about how bone fractures heal. The present invention further introduces an entirely new science to bone healing. That is, as explained with regard to the preferred embodiment, the selection of the bioresorbable material determines its compressibility curve as a function of resorption time. Different bioresorbable materials have different compressibility curves, affecting the dynamization seen at the fracture site 66. Different spacer geometries and different bone fastener locations and geometries also affect the dynamization (tensile, compressive and bending) seen at the fracture site 66. The present invention will allow a new body of data to be gathered on the effectiveness of bone fracture healing under different dynamization conditions. Based on this data, future changes may be made to further improve the invention, or to modify the invention for particular bone or fracture conditions. For instance, not only may a different bioresorbable material be used to change the compressibility curve, but a combination of bioresorbable materials may be used. Composite bioresorbable materials may be formed to combine compressibility characteristics, or the spacer(s) 46 may be formed of two or more distinct bioresorbable materials. The thickness of these two or more materials may be selected to engineer the desired compressibility curve of the spacer 46 and thereby provide the most beneficial dynamization characteristics. The bone fastener 48 may be positioned in the dynamization window 44 between a proximal spacer portion of one material and a distal spacer portion of a second material so as to have tensile dynamization characteristics which differ from compressive dynamization characteristics. The spacers 46 in opposing windows 44 may be of different sizes or formed of different bioresorbable materials to control the bending dynamization relative to the tensile and compressive dynamization. The present invention thus allows controlled dynamization across the fracture site 66, both for improving fracture healing and for learning more about how dynamization affects the healing of the fracture.

The preferred PLA material does not include any active agents for release during bioresorption. Alternatively, the bioresorbable material may include an active agent as desired for release adjacent the fracture site, such as an antibiotic or a growth factor.

Although the present invention has been described with reference to preferred embodiments, workers skilled in the art will recognize that changes may be made in form and detail without departing from the spirit and scope of the invention. For instance, while all of the these attachments methods have been described with regard to the preferred bicortical attachment, unicortical attachment can also be used with a shorter bone fastener or by only advancing the bone fastener partially through the nail 20.

What is claimed is:

1. A bone support assembly for treatment of a bone, comprising:
   a bone support implant formed of a non-resorbable material, the bone support implant having a first window extending therethrough, the first window having a first window shape; and
   a first insert formed of a non-metal material separately from the bone support implant, the first insert having outer dimensions which correspond to the first window shape, such that the first insert is insertable into the first window and received by the first window to secure the first insert relative to the bone support implant.

2. The bone support assembly of claim 1, wherein the non-metal material of the first insert is a bioresorbable material.

3. The bone support assembly of claim 1, further comprising:
   a bone fastener having a length sufficient to extend through the first insert in attachment with a bone, the bone fastener having a width small enough to be received in the insert and through the first window, wherein the bone fastener is insertable through the insert when the insert is in the first window to attach the bone support implant relative to a bone, with the direction of insertion of the bone fastener in the insert being in the same direction as the insert is insertable into the bone support implant.

4. The bone support assembly of claim 3, wherein the outer dimensions of the first insert are sized to be received in the first window with a press fit.

5. The bone support assembly of claim 3, wherein the outer dimensions of the first insert are sized to be received in the first window with a snap fit.

6. The bone support assembly of claim 1, wherein the first window defines a window axis, and wherein the first window comprises:
   a neck portion through which at least a major portion of the first insert may pass; and
   a mouth portion which extends from the neck portion and defines a widening opening relative to the window axis, the mouth portion extending at a different angle relative to the window axis than the neck portion.

7. The bone support assembly of claim 1, wherein the first insert defines an insertion axis, and wherein the first insert has a contact surface which, during insertion into the first window, makes sliding contact with the bone support implant, the contact surface comprising:
   a leading portion extending at a first angle relative to the insertion axis; and
   a trailing portion extending at a second, different angle relative to the insertion axis.

8. The bone support assembly of claim 7, wherein the trailing portion defines a widening profile relative to the insertion axis.

9. The bone support assembly of claim 1, wherein the first insert defines a first insert axis defined in a direction of insertion into the bone support implant, the first insert having a contact surface which contacts the bone support implant during or after insertion, the contact surface comprising:
   a first portion extending generally parallel to the first insert axis; and
   a second portion extending at an angle relative to the first portion, the second portion being wider than the first portion.

10. The bone support assembly of claim 1, wherein the first insert is packaged in a sealed container for prolonged shelf-life and sealing the insert separate from the bone support implant, the sealed container substantially preventing the first insert from contacting air.

11. The bone support assembly of claim 10, wherein the sealed container comprises:
    a sealed inner pouch; and
    a sealed outer pouch surrounding the sealed inner pouch.

12. The bone support assembly of claim 10, wherein the inner pouch is formed of a material from the group consisting of PET, foil and polyethylene, and wherein the outer pouch is formed of a material from the group consisting of paper, polyester and polyethylene.

13. The bone support assembly of claim 10, wherein the non-metal material is a bioresorbable material which has been sterilized by Cobalt 60 Gamma irradiation, Ethylene Oxide sterilization or gas plasma sterilization.

14. The bone support assembly of claim 10, wherein the sealed container is flushed with nitrogen upon sealing, such that the insert is retained in a nitrogen environment for prolonged shelf-life.

15. The bone support assembly of claim 10, wherein the sealed container shields the insert from light.

16. A bone support assembly for treatment of a bone, comprising:
    a bone support implant formed of a non-resorbable material, the bone support implant having a first window extending therethrough, the first window having a first window shape; and
    a first insert formed of a non-metal material separately from the bone support implant, the first insert having outer dimensions which correspond to the first window shape, such that the first insert is insertable into the first window and received by the first window to secure the first insert relative to the bone support implant; and
    a second insert formed of a non-metal material separately from the bone support implant and separately from the first insert, the second insert having outer dimensions which correspond to the first window shape, such that the second insert is insertable into the first window and received by the first window to secure the second insert relative to the bone support implant, the second insert having different mechanical or chemical treatment properties than the first insert.

17. The bone support assembly of claim 16, wherein the different mechanical or chemical treatment properties are selected from the group consisting of: different hardness, different rates of absorption, different active agents and different amounts of active agents.

18. A bone support assembly for treatment of a bone, comprising:
    a bone support implant formed of a nonresorbable material, the bone support implant having at least one window defined therein for exposure of a selected spacer;
    a first spacer formed of a non-metal material, the first spacer being sized such that it is receivable in the window in an exposed position for transverse fastening through the bone support implant and through the first spacer with a bone fastener; and a second spacer formed separately from the first spacer, the second spacer being sized such that it is receivable in the window in an exposed position for transverse fastening through the bone support implant and through the second spacer with a bone fastener, the second spacer having different mechanical or chemical treatment properties than the first spacer.

19. The bone support assembly of claim 18, wherein the bone support implant is an intramedullary nail for insertion into the medullary canal of a bone.

20. The bone support assembly of claim 18, wherein the bone support implant is a bone plate for placement adjacent a bone.

21. The bone support assembly of claim 18, wherein an additional bone attachment hole is defined in the bone support implant, the additional bone attachment hole being left open for insertion of a bone fastener therethrough.

22. The bone support assembly of claim 18, further comprising:

a bone fastener having a length sufficient to extend through the first insert in attachment with a bone, the bone fastener having a width small enough to be received in the insert and through the first window.

23. The bone support assembly of claim 18, wherein either the first insert or the second insert fills the first window prior to anchoring of a bone fastener transversely through the first insert.

24. The bone support assembly of claim 18, wherein the different mechanical or chemical treatment properties are selected from the group consisting of: different hardness, different rates of absorption, different active agents and different amounts of active agents.

25. A bone support assembly for treatment of a bone, comprising:

a bone support implant formed of a non-resorbable material, the bone support implant having a first attachment surface having a first attachment surface shape; and a first insert formed of a non-metal material separately from the bone support implant, the first insert having outer dimensions which correspond to the first attachment surface shape of the bone support implant, such that the first insert is attachable to the bone support implant with the outer dimensions of the first insert in a mating attachment with the first attachment surface to secure the first insert relative to the bone support implant; and a second insert formed of a non-metal material separately from the bone support implant and separately from the first insert, the second insert having outer dimensions which correspond to the first attachment surface shape, such that the second insert is attachable to the bone support implant with the outer dimensions of the second insert in a mating attachment with the first attachment surface to secure the second insert relative to the bone support implant, the second insert having different mechanical or chemical treatment properties than the first insert.

26. The bone support assembly of claim 25, wherein the outer dimensions of each of the first insert and the second insert are sized to be attached to the first attachment surface with a press fit.

27. The bone support assembly of claim 25, wherein the outer dimensions of each of the first insert and the second insert are sized to be attached to the first attachment surface with a snap fit.

28. The bone support assembly of claim 25, wherein the bone support implant is formed of metal and wherein the first and second inserts are formed of bioresorbable materials.

* * * * *